(12) United States Patent
Glazer et al.

(10) Patent No.: US 9,586,244 B2
(45) Date of Patent: Mar. 7, 2017

(54) SYSTEM AND METHOD FOR PROCESSING WASTE MATERIAL

(71) Applicant: Red Bag Solutions, Baltimore, MD (US)

(72) Inventors: Sanford Glazer, Potomac, MD (US); William D. Norton, Hunt Valley, MD (US)

(73) Assignee: Red Bag Solutions, Baltimore, MD (US)

( * ) Notice: Subject to any disclaimer, the term of this patent is extended or adjusted under 35 U.S.C. 154(b) by 93 days.

(21) Appl. No.: 14/182,624

(22) Filed: Feb. 18, 2014

(65) Prior Publication Data

US 2014/0234165 A1 Aug. 21, 2014

Related U.S. Application Data

(60) Continuation-in-part of application No. 13/859,148, filed on Apr. 9, 2013, now Pat. No. 8,652,404, which is a division of application No. 13/099,073, filed on May 2, 2011, now Pat. No. 8,425,857.

(60) Provisional application No. 61/330,327, filed on May 1, 2010.

(51) Int. Cl.
| | |
|---|---|
| *B09B 3/00* | (2006.01) |
| *A61L 2/18* | (2006.01) |
| *A61L 2/20* | (2006.01) |
| *A61L 11/00* | (2006.01) |

(52) U.S. Cl.
CPC ............ *B09B 3/0083* (2013.01); *A61L 2/183* (2013.01); *A61L 2/202* (2013.01); *A61L 11/00* (2013.01); *B09B 3/0075* (2013.01)

(58) Field of Classification Search
CPC ................................ B09B 3/00; B09B 3/0075
USPC ..................................................... 422/38, 291
See application file for complete search history.

(56) References Cited

U.S. PATENT DOCUMENTS

| | | |
|---|---|---|
| 3,310,241 A | 3/1967 | Wandel |
| 5,277,869 A | 1/1994 | Glazer et al. |
| 5,427,737 A | 6/1995 | Glazer et al. |
| 5,431,861 A | 7/1995 | Nagahiro et al. |
| 5,582,793 A | 12/1996 | Glazer et al. |
| 6,605,750 B1 | 8/2003 | Bessho et al. |
| 6,955,758 B2 | 10/2005 | Yamazaki et al. |

(Continued)

OTHER PUBLICATIONS

International Search Report and Written Opinion of the International Searching Authority issued in International Application No. PCT/US2012/031974 dated Jul. 6, 2012.

*Primary Examiner* — Sean E Conley
(74) *Attorney, Agent, or Firm* — Venable, LLP

(57) ABSTRACT

A waste processing system includes a receptacle for waste material, including bags of waste, and a liquid to be mixed with the waste. The receptacle has an inlet, a waste outlet, and at least one nozzle opening with at least one slicing nozzle that sprays a slicing fluid under pressure sufficient to manipulate the waste material. The system includes a pump for chopping the waste material and circulating and mixing the liquid and waste material, a waste inlet conduit, and a waste outlet conduit. The receptacle, pump, waste inlet and waste outlet conduits define a closed, pressurized waste processing circuit for circulating the liquid and waste. The system also includes a heating system to heat the liquid and waste to effect biological neutralization of the liquid and waste material, and all surfaces of the waste processing system with which the waste material being processed comes into contact.

44 Claims, 28 Drawing Sheets

(56) References Cited

U.S. PATENT DOCUMENTS

2006/0124541 A1 6/2006 Logan et al.
2009/0087317 A1 4/2009 Keener
2011/0155257 A1 6/2011 Sundholm

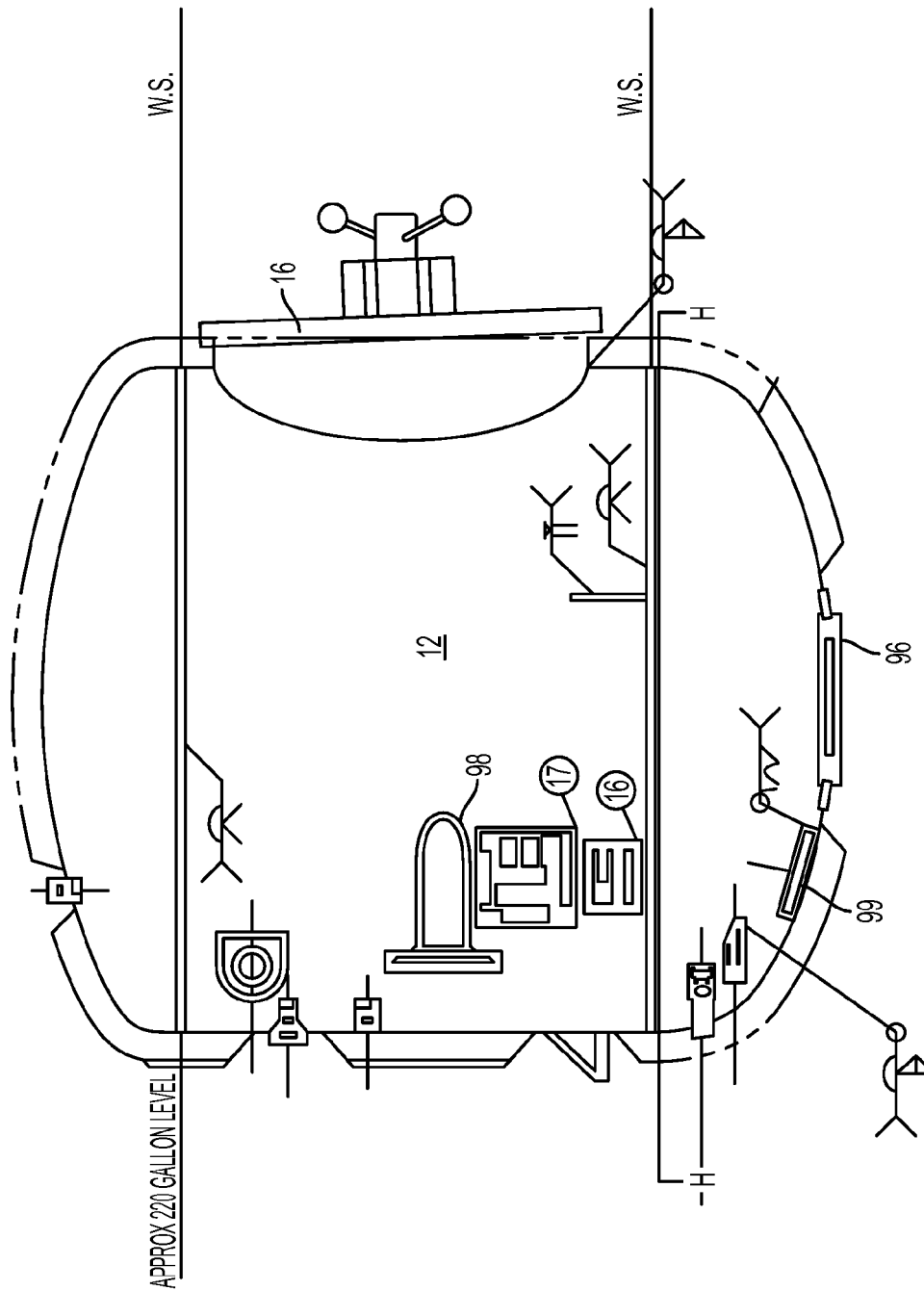

PLAN VIEW

BOTTOM HEAD VIEW
SECTION H-H

DETAIL F
WELDMENT
M.F. = 2

OSS PROCESSING
CONTROL STAGES

| | NAME | DESCRIPTION | RECOVER TO STAGE |
|---|---|---|---|
| 302 | INITIAL STAGE | INITIALIZE, OZONE GENERATOR | |
| 304 | SLEEP | KEEP UNIT LOCKED SO IT CANNOT BE STARTED | INITIAL STAGE |
| 306 | READY-TO-START | UNIT READY FOR PROCESS TANK DOOR TO BE CLOSED AND START BUTTON TO BE PUSHED | INITIAL STAGE |
| 308 | OZONATE | FILL PROCESS TANK WITH OZONE GAS | INITIAL STAGE |
| 310 | FILL | FILL PROCESS TANK WITH OZONATED WATER | OZONATE |
| 312 | GRIND | CHOP AND RECIRCULATE MATERIAL | FILL |
| 314 | STERILIZE | CALCULATE STERILIZATION TIME BASED ON O3 CONCENTRATION AND TIME AS MATERIAL CONTINUES TO BE CIRCULATED | GRIND |
| 316 | VENT | VENTING AIR FROM PROCESS TANK TO ATMOSPHERE | STERILIZE |
| 318 | DISCHARGE | DISCHARGE CONTENTS OF PROCESS TANK INTO SEPARATOR | VENTING |
| 320 | RINSE | RINSE PROCESS TANK WITH WATER FROM FACILITY | DISCHARGE |
| 322 | DRAIN | DRAIN PROCESS TANK AND SEPARATOR | RINSE |
| 324 | COMPLETE | PRINT REPORT AND STORE HISTORIES | DRAIN |

FIG. 13

SYSTEM AND METHOD FOR PROCESSING WASTE MATERIAL

CROSS-REFERENCE TO RELATED APPLICATIONS

This application is a continuation-in-part of and claims the benefit of U.S. patent application Ser. No. 13/859,148, filed Apr. 9, 2013, now U.S. Pat. No. 8,652,404, which is a divisional of and claims the benefit of U.S. patent application Ser. No. 13/099,073, filed May 2, 2011, now U.S. Pat. No. 8,425,857, which claims benefit under 35 U.S.C. §119 (e) of U.S. Provisional Patent Application No. 61/330,327, filed on May 1, 2010, the content of each of which is expressly incorporated herein by reference in its entirety.

BACKGROUND

Field of the Invention

The present invention relates generally to systems and methods for processing waste material, and more particularly to such systems and methods which may not only effect the sterilization and optionally, disinfection, of waste material such as medical (also known as "red bag"), food, disposable diapers, and other types of waste, but also reduce the volume of such waste material, and dispose of water soluble polymeric or fibrous waste material.

Waste management evolved in the latter part of the twentieth century into an industry of considerable importance, as societal and environmental attention had focused on the conventional processes by which waste has to date been handled for disposal. These conventional waste disposal processes included incineration, dumping at sea, and burial in landfills. Each of these processes, however, is encumbered by significant societal and environmental disadvantages and regulatory restrictions.

Incineration is objectionable due to its attendant chemical and particulate pollution of the atmosphere and surrounding locales. Further, these pollutants can be transported over great distances by prevailing winds, thereby extending the scope of environmental impact beyond the immediate locale of the incinerator. Waste disposal in the oceans is objectionable due to its adverse environmental impact on sea life and coastal shores. Landfills are objectionable due to their attendant spatial demands, offensive odors, contamination of ground water and potential for production of hazardous substances arising from the mixing and interaction of buried materials.

Spatial considerations are especially prevalent in urban centers, where population growth has resulted in suburban expansion to locations well outside of the urban center, necessitating in some instances in the relocation of existing landfills and the creation of costly new landfills at locations geographically remote from the centers they serve. Disposable diapers, for example, have proven to be an increasing problem for municipal disposal.

Additional waste disposal problems arise in view of the type of waste that is to be disposed. For example, special precautions are required for the disposal of biological and medical waste due to the overwhelming concern for preventing the creation and/or spread of infectious disease. Further concerns arise due to the presence of extremely sharp medical instruments such as needles, knives, and broken glass containers that can cut or lacerate the skin of personnel and animals with which the waste comes in contact, thereby presenting both a risk of physical harm and biological contamination. For these reasons, such waste is typically thermally or chemically treated and buried in dedicated medical waste disposal facilities. The treatment should be of a type that renders the waste biologically neutral or inert.

Sterilization can typically be accomplished by any one of a variety of prescribed chemical and non-combustion thermal treatment regimens, as well as incineration or autoclaving. Chemical sterilization generally provides for exposure of the waste material to an antiseptic solution such as liquid chlorine for a prescribed time interval; however, the use of chemical sterilizing agents presents disposal problems for the liquid following waste treatment due to the toxicity of chlorine and other antiseptic solutions.

An alternative to chemical sterilization is autoclaving. Autoclaving provides for exposure of the waste to heat at upwards of 250° F. (121° C.) at 15 pounds per square inch ("PSI") for 15-40 minutes. While sterilization can be accomplished in both dry air and steam environments, steam autoclaving is generally preferred due to its greater penetrating capabilities (especially important for sterilizing "soft" waste such as textiles and gauze) and its lethality via the process of denaturation. Longer periods are used to assure steam penetration of heavy, fluid-absorbable loads. Faster processing can be accomplished for some waste materials by increasing temperature and pressure. However, a significant disadvantage of steam autoclaving without reducing the size of the material is its failure to assure complete penetration of the waste and its exposure to the heat contained within the water vapor. Further disadvantages include the tendency for autoclaves (both steam and dry) to stratify and to trap comparatively cool air in pockets, thereby precluding sterilization. In addition, the waste is neither reduced in volume or in mass; instead, mass can increase in some instances (i.e., textiles and gauze) due to the absorption of water vapor, thereby exacerbating the problem of waste disposal referenced above.

The above treatment systems may be used to process waste that is provided in containers (e.g., medical red bag waste). However, such bagged or otherwise sealed waste may not be effectively treated due to the presence of the container, which can potentially prevent thermal or chemical treatments from penetrating the waste contained therein. Such containers can be opened to empty the waste, but such additional steps to open containers may delay the processing of the waste, and increase costs. Additionally, precautions must be taken to safely empty the waste from the containers and into a treatment system.

In view of the foregoing, there is a pressing societal need to not only reduce the volume of waste material that is produced, but also to more effectively and efficiently process the waste so that it has a diminished environmental impact. This need is especially pressing in instances where waste is produced in bulk, as can occur in hospitals, clinical laboratories, research facilities, nursing homes, restaurants, and the like.

While efforts are being undertaken to reduce waste production, these efforts alone will not eliminate the various problems associated with waste disposal, particularly in the medical and dental industries, where single patient use (i.e., non-reusable) surgical instruments have gained widespread acceptance due to concerns over spread of the family of hepatitis viruses and HIV.

Moreover, it would be preferable to provide systems and methods for processing waste material at a lower cost, environmentally and economically.

SUMMARY

Accordingly, it is an object of the present invention to provide a system and method for sterilizing medical and other forms of waste. Another object of the invention, when waste is in a bulk form, may be to reduce the volume of waste solids for disposal. It is a further object of the present invention to provide a system and method for treating water-soluble polymeric or fibrous waste material. It is a further object of the present invention to provide a system and method for opening containers and emptying the waste from the opened containers.

According to one embodiment, a waste disposal system and/or method is directed to optimally sterilizing waste and to reducing the volume of waste solids, thereby simplifying procedures for waste disposal and reducing the demand for disposal space in landfills. While embodiments of the present invention may be particularly advantageous for use in processing bulk medical waste in the form of aggregate or "red-bagged" medical waste along with non-aggregate medical waste, its principles may be equally applicable for the treatment of other forms of waste including contaminated liquid waste and items such as food waste produced incident to the operation of restaurants and so-called "fast food" establishments.

According to another embodiment, the system and/or method can also be used for processing disposable diapers. In this latter regard, waste treatment in accordance with the teachings herein greatly reduces the organic content of the waste solids, thereby resulting in a diminution of rodent and other pest infestation typically associated with food waste disposal as well as the capacity requirements for waste receptacles (i.e., "dumpsters") on-site at the restaurant. Alternatively, the principles of the invention may be applied to the disposal of water soluble polymeric or fibrous waste materials, whereby treatment results in the dissolution of the waste material.

According to a further embodiment, a closed waste processing system may be provided that is operable to effect biological neutralization of waste by a process of waste sterilization. An ozone system can optionally be provided that is operable through appropriate valve apparatus to deliver ozone gas, ozonated water and/or other suitable ozonated and/or disinfecting fluids to a process tank, also known as a decontamination chamber, to mix with the waste material as it is drawn toward a cartridge/cartridge/macerator pump, also known as a waste processing chopper/pump assembly, positioned downstream from the process tank. Alternatively, the ozonated water may be produced directly within the process tank, where the water and/or fluid can be supplied from a supply line such as a hot or cold water line and the ozone can be supplied from an ozone generator. In one embodiment, the ozonated fluid is water. However, the principles of the present invention are applicable for other liquids.

According to one embodiment, output from the pump may be directed to the process tank and may circulate there-through in a closed circuit in a continuous manner, during which time the waste solids are ground by the cartridge/cartridge/macerator pump to successively finer particles and mixed with the circulating ozonated fluid in the processing tank.

According to another embodiment, the waste and fluid mixture may be oxygenated to an ozone concentration range 5-50% and a temperature of about 85° F. to about 165° F. within the process tank and directed to a high-capacity cartridge/cartridge/macerator pump, which may grind the waste to further reduce its volume and return the fluid and entrained ground waste to the process tank for continued processing. The fluid and entrained waste may be continuously processed and circulated by the cartridge/cartridge/macerator pump and oxygenated to the requisite processing concentration within a closed loop that extends from the process tank to the cartridge/cartridge/macerator pump and back to the process tank for a prescribed time interval to ensure processing to a desired level of biological neutralization.

According to another embodiment, operation of the system may be monitored by various sensors having a suitable output to appropriate control apparatus to ensure processing of the waste in a fail-safe manner. A record can optionally be rendered which details operation of the system as a function of time, concentration and temperature. Processed waste can optionally be filtered to separate solids in excess of prescribed dimension to permit for drying of the solids by suitable dehydration apparatus. Processed waste solids can optionally be compacted by suitable compacting apparatus to further reduce waste volume. The mixture of processing fluid and liquid waste can be passed into a sanitary sewer for disposal to meet municipal requirements. In a further embodiment, a portion of the processing fluid and liquid waste may be collected following processing and returned to the decontamination chamber prior to cooling for use in processing of another waste processing cycle, thereby further reducing waste production and energy requirements for the waste processing system.

According to another embodiment, a closed, pressurized waste processing system is provided that is operable to effect biological neutralization of waste by a process of waste sterilization. As used herein, the term "system" includes both methods and apparatus for effecting the desired form of waste treatment. The system provides for receipt of the waste in a decontamination chamber which is sealable by a removable and pressurizable cover. A reservoir is provided and is operable through appropriate valve apparatus to deliver water or other suitable fluids to the flow of waste material as it is drawn toward a waste processing chopper/pump assembly positioned downstream from the decontamination chamber. Preferably, the fluid is water and is stored within the reservoir at an elevated temperature of on the order of about 170.degree. F. (77.degree. C.) so as to expedite processing. A selectively-actuable gate can be provided in the line between the decontamination chamber and the chopper/pump to inhibit the flow of waste solids to the chopper/pump until it attains its optimal operating speed, at which point the gate can be opened to permit the fluid and solids stored in the chamber to flow to the chopper/pump for processing thereby. Output from the pump is directed to the decontamination chamber and circulates therethrough in a closed, pressurized circuit in a continuous manner, during which time the waste solids are ground by the chopper/pump to successively finer particles and mixed with the circulating fluid from the reservoir. Suitable heating means is associated with the decontamination chamber to effect heating of the fluid and entrained waste solids to the requisite temperature to effect disinfection or sterilization as these materials are circulated by the pump for the desired period of time. Sterilization can be implemented by elevating the temperature of the circulating waste and fluid mixture to a temperature of at least 270.degree. F. (132.degree. C.) and maintaining that temperature for a time interval of at least six minutes. Temperature sensors are preferably provided along the fluid flow path to provide an indication of circulated fluid temperature throughout system operation and to ensure that the requisite processing temperature has been maintained for the required time interval. Once the waste material has been ground by the pump and exposed to the heated water for the prescribed period of time, the water and entrained waste particulates are directed to a receiving tank that is substantially filled with tap water at ambient temperature for cooling to a prescribed minimum temperature so as to permit for disposal of the liquid portion of the mixture into the municipal waste disposal system. Cooling of the processed waste can be expedited by introducing cool water from the receiving tank into the circulating stream of sterilized waste material. Although the waste will no longer be "biologically neutral" following its mixture with the tap water, the waste material will nevertheless be biologically and physically safe for disposal, as it will have a biological activity attributable only to that of the tap water with which it is mixed. The ground waste solids can be filtered from the processed waste and disposed of in a conventional manner, whereas the waste liquids can be passed (following cooling) into the municipal sewer lines.

In a further aspect of the invention, waste processing in the foregoing manner is electronically controlled in accordance with a pre-established system program. However, variables such as pump speed, fluid flow rate and duration of operation can be selected within prescribed ranges in accordance with such factors as the nature and quantity of waste to be treated. Further parameters which affect waste processing include the dimensions of the conduits through which processed material and fluid flow. Preferably, the foregoing variables and parameters are selected to provide for the production of processed waste solids of a size in the range of from about 1/16 in. (1.5 mm) to about 1/4 in. (6.5 mm) in their largest dimension. A printout of system operation parameters such as waste temperature throughout the processing procedure can optionally be provided to render a permanent record of system operation. Alternatively, or in conjunction with printer operation, the various above-referenced operation parameters can be stored in electronic memory for subsequent recall and display on a visually perceptible device such as a cathode ray tube (CRT) or similar display of alpha-numeric and graphic data. In all instances, however, waste processing proceeds for a period of time which provides for grinding and exposure of the waste to a circulating stream of superheated water for a period of time that meets or exceeds the applicable standards and regulations governing material disinfection and sterilization in accordance with the selected form of waste treatment.

According to an embodiment, a waste processing system includes a receptacle for receiving waste material, including bags of waste, and a liquid to be mixed with the waste material. The receptacle has an inlet, a waste outlet, and at least one nozzle opening. The waste processing system also includes at least one slicing nozzle that sprays a slicing fluid under pressure into the receptacle via the at least one nozzle opening, and a pressure system that pressurizes the slicing fluid. The pressure system and the at least one slicing nozzle produce a spray sufficient to manipulate the waste material. The system further includes a pump for chopping the waste material and circulating and mixing the liquid and waste material, the pump having a pump inlet and an outlet. The system further includes a waste inlet conduit extending between the waste outlet and the pump inlet, and a waste outlet conduit extending between the pump outlet and the receptacle inlet. The receptacle, pump, waste inlet and waste outlet conduits may define a closed, pressurized waste processing circuit through which the mixed liquid and waste material can be circulated. The system further includes a heating system to heat the mixture of the liquid and the waste material to a temperature in excess of the boiling point of the liquid at standard pressure, the temperature being sufficient to effect biological neutralization of the mixed liquid and waste material, and all surfaces of the waste processing system with which the waste material comes into contact being processed to attain said biological neutralization.

BRIEF DESCRIPTION OF THE DRAWINGS

These and other objects and advantages of the present invention will become apparent from the following specification when read in conjunction with the accompanying drawings, wherein like reference numerals/characters represent like or corresponding parts throughout the various views:

FIGS. 11A-11E depict various views of connections to the process tank, according to an embodiment of the present invention;

FIG. 13 is a chart showing various control stages of the ozone sterilization system, according to an embodiment of the present invention.

DETAILED DESCRIPTION

Figure 1:
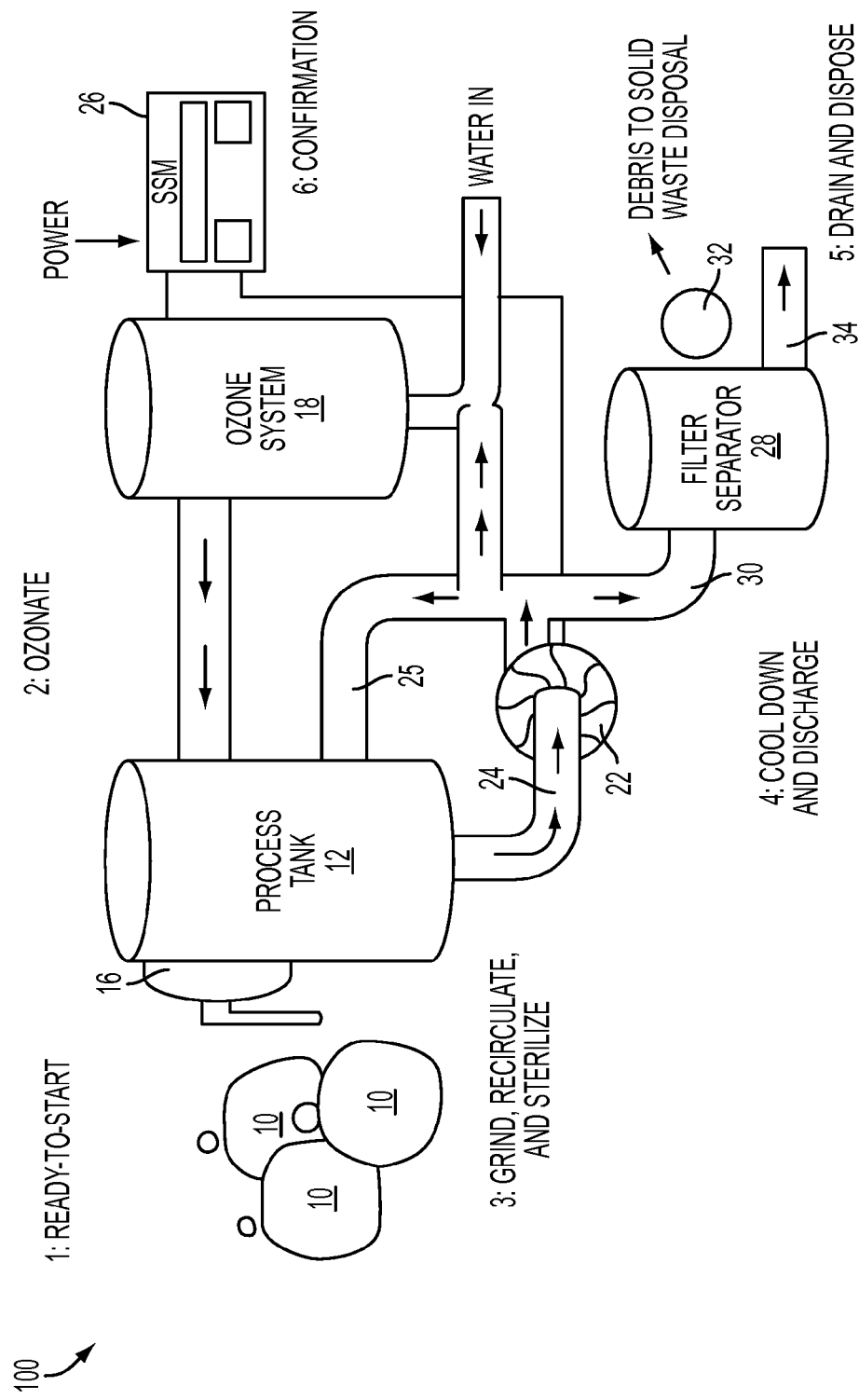
FIG. 1 is a system diagram of the ozone sterilization system, in accordance with an embodiment of the present invention.

The various embodiments of the invention are discussed in detail below. While specific embodiments are discussed, it should be understood that this is done for illustration purposes only. In describing and illustrating the embodiments, specific terminology is employed for the sake of clarity. The embodiments so disclosed, however, are not intended to be limited to the specific terminology selected. Persons of ordinary skill in the relevant and related art will recognize that other components and configurations may be used without departing from the true spirit and scope of the embodiments. It is to be understood that each specific element includes all technical equivalents that operate in a similar manner to accomplish a similar purpose. Therefore, the examples and embodiments described herein are non-limiting examples.

Generally, the term "disinfection" and its variants pertains to the destruction of pathogenic microorganisms or their toxins or vectors. The term "sterilization" and its variations pertains to the destruction of all living microorganisms and their spores, thereby rendering the material so processed void of all living matter. For the purposes of this application, the term "maceration" refers to cutting up and shredding waste material while the waste material is immersed in an ozonated liquid.

Ozone is a chemically active radical species of oxygen, commonly produced by ionization of either air or pure oxygen. Ozone includes disinfecting properties, and may be used as a sterilizing agent in certain applications. Ozone is considered very safe as evidenced by the approval of the U.S. Food and. Drug Administration for use in treating food products. Unlike conventional disinfecting chemicals, ozone does not form hazardous disinfectant by-products that are harmful to the environment or are toxic to animals and humans. Once ozone has fully reacted with substances in water or air, excess gas decomposes quickly to normal oxygen and is reabsorbed into the atmosphere. Commercial ozone generators are readily available, and economically produce significant amounts of ozone.

For purposes of this application, the term "needle-like spray" defines a substantially focused or non-dispersed spray (i.e., having a substantially straight and thin profile).

Systems and methods of processing waste material in accordance with the various embodiments of the present invention, as described below, may be comprised in a similar manner as those shown and described in U.S. Pat. No. 5,277,869 (Glazer et al.), U.S. Pat. No. 5,427,737 (Glazer et al.), and U.S. Pat. No. 5,582,793 (Glazer et al.).

It has been found that by using ozone in the manner shown and described herein below according to some embodiments, hot water, steam, and boiler components may be eliminated. This not only reduces the overall cost of manufacturing such systems, but also reduces the amount of water and electricity used in the process and, thereby reduces the operating costs. Other benefits of the present invention include the discontinuance of needing an ASME-certified tank, thereby avoiding altogether the complexity and expense associated with the construction of ASME-certified, pressurized systems; elimination of other unnecessary components as a result of removing the hot water, steam, and boiler components; greater capacity due to short cycle times; and a smaller footprint not only makes it easier to manufacture and lighter to transport, but also enables a portable embodiment of systems according to the present invention.

With reference now to the drawings, FIG. 1 depicts a system diagram of the ozone sterilization system (OSS) 100 in accordance with an embodiment of the present invention. In FIG. 1, regulated medical waste (RMW) 10, bagged or otherwise contained and sealed, may be placed within a process tank 12 for sterilization. Such waste can be in the form of virtually any type of non-toxic inorganic or organic material, such as medical waste, food waste, rubber, plastics, and the like for which it is desirable to disinfect, or optimally render biologically neutral (i.e., biologically inert or devoid of living organisms) via sterilization. Medical waste can include, by way of non-limiting example, sharps such as needles, knives and blades, trocars, clamps, glass containers, gauze and bandages, surgical gloves and gowns, and various other instruments and paraphernalia which contacts internal body fluids such as blood, lymphatic, semen, and vaginal fluids. It may also include sharps containers containing such waste. Medical waste can also include, for example, small research animals, animal bedding, plastic animal cages, animal and human pathological waste and egg embryos. Waste sterilization is preferred in instances such as with some forms of medical waste where bacteria, viruses and/or spores may be present, in which case all living organisms associated with the waste must be destroyed prior to its disposal.

The amount of RMW 10 placed within the process tank 12 should be of an appropriate size, for example, between 75 and 200 pounds of waste. Once loaded, the door gasket 14 (See FIG. 2) of the process tank 12 may be wiped clean and the door 16 of the process tank 12 may be closed and secured.

An ozone system 18 may be connected to the process tank 12 via supply line 20. The ozone system 18 may inject ozonated water, as well as ozone gas, into the process tank 12 to mix with the RMW 10. The ozonated water may be produced from hot or cold water tap water. The combination of the ozonated water and RMW 10 is referred to as "slurry."

Ozone is about 13 times more soluble than oxygen in water at standard temperature and pressure. It is readily decomposed back to oxygen, from which it is formed. This decomposition is very rapid in the presence of ozone demanding impurities, i.e., in water, but is slower in high purity water or in the gaseous phase. Turbulence or churning of ozonated water by, for example, a pump, may further cause the ozone to decompose back into oxygen. Therefore, in order to compensate for the decomposition of the ozonated water in the process tank 12, the ozone system 18 may deliver additional ozone gas into process tank 12 throughout the duration of the sterilization process to maintain a particular concentration of ozone in the slurry. As discussed below, a sensor may monitor the ozone concentration of the slurry.

Ozone is produced from dried air or from oxygen. The conversion of oxygen into ozone requires the rupture of the very stable bond of the oxygen molecule. This is accomplished commercially by passing a clean dry, oxygen-containing gas through an electrical discharge. In this method, high voltage is applied across a discharge gap and collisions occur between electrons and oxygen molecules. A fraction of these electrons have sufficient kinetic energy (around 6 or 7 eV) to dissociate the oxygen molecule to form ozone, while the remaining electrons release their energy as heat.

Ozone generators may be assembled with modular electrodes and electronics; reducing the number and cost of spare parts. The ozone generators may be fully assembled and factory tested. They may include mechanical, electrical and instrument fittings. According to one embodiment, the ozone system 18 may be a "corona discharge" generator, whereby lined glass or ceramic dielectric tubes, are fitted inside water cooled stainless steel tubes and provided with a gap, "discharge gap", between the two surfaces. Gas may be passed through the annulus (discharge gap) and a high voltage passed across the gap through the gas results in ozone generation. According to another embodiment, the ozone system 18 may be a MCP series ozone generator. The MCP series is a new line of high technology ozone generators that are compact, inexpensive and easy to use.

According to a further embodiment, the ozonated water and gas may be produced directly within the process tank 12. In this embodiment, water and/or another suitable fluid may be supplied from a supply line such as a hot or cold water line and the ozone gas may be supplied directly by an ozone generator into the process tank 12. The water and ozone gas may mix within the process tank 12 to produce ozonated water having a particular concentration.

In one embodiment, approximately 60 gallons of ozonated water may be injected from the ozone system 18 into the process tank 12. The ozonated water from the ozone system 18 may mix with the RMW 10 placed within the process tank 12 for a pre-determined duration of time.

According to one embodiment, the OSS 100 may also be particularly useful for effecting sterilization of virtually all forms of non-toxic waste by exposing the waste to, for example, water ozonated to an ozone concentration range of approximately 5-50% and heated to a temperature of about 85° F. to about 165° F. within the process tank 12. The ozonated water may be produced from standard hot tap water.

According to another embodiment, sterilization may be implemented by elevating percentage of ozone concentration in the liquid mixture to about 20% and maintaining that concentration for a time interval of about eight minutes. A dissolved ozone analyzer and ambient ozone analyzer may be provided to monitor the ozone concentration. Temperature sensors may be provided along the fluid flow path to provide an indication of circulated fluid temperature throughout system operation and to ensure that the requisite processing temperature has been maintained for the required time interval.

A maceration (chopper) pump 22 may be connected to the process tank 12 via pipe 24. The cartridge/cartridge/macerator pump 22 may be generally comprised of a cutter assembly and a pump assembly (See FIG. 7 for details). The cartridge/macerator pump 22 may include multiple cutting surfaces to separate and reduce the size of the RMW 10 into smaller particles while the RMW 10 remains completely exposed to the ozonated water in the slurry.

The cartridge/macerator pump 22 may continuously recirculate the slurry through a circulation loop 25 back into the process tank 12 and back through the multiple cutting surfaces of the cartridge/macerator pump 22 until the RMW debris particles are of a sufficiently small size and the proper ozone saturation and duration of sterilization treatment is complete. The term "continuously" refers to the cycling of the slurry between the process tank 12 and the cartridge/macerator pump 22 until the slurry is sterilized. There may, however, be intermittent pauses or gaps in the cycling, as long as the overall goal of sterilization is achieved.

According to one embodiment, appropriate size of the RMW particles may be determined by the amperage of the 15 HP chopper pump and the amount of time the cycle has been operating. According to one embodiment, the RMW particles may have a size in the range of about 1/16 in. (1.5 mm) to about 1/4 in. (6.5 mm) in their largest dimension.

In another embodiment, the cartridge/macerator pump 22 may be slowed before the ozonated water is introduced into the process tank 12. The ozonated water may be mixed in a closed circuit with the RMW 10, and allowed to react for a predetermined period of time. For example, while this time may be about 6 minutes for typical batches of about 80 pounds of waste to from 75 to about 100 gallons of water, this time may be varied as a function of the temperature of the slurry and concentration of ozone used. Such water may be cold or hot water in a temperature range of about 85° F. to about 165° F. The concentration of ozone in the ozonated water may be from about 5% to about 50%.

According to another embodiment, once the waste material has been ground by the pump and exposed to ozone for the prescribed period of time, the water and entrained waste particulate may be checked for ozone concentration so as to permit for disposal of the liquid portion of the mixture into the municipal waste disposal system. For example, an operating system 26, including residual and ambient analyzers, may monitor the sterilized waste material to see that any remaining ozone has been reduced to oxygen prior to discharge of the waste from the process tank 12.

Once properly sterilized, may be discharged via pipe 30 to a filter separator 28. The filter separator 28 may filter or separate the solids from the liquids of the sterilized waste. The entrained waste solids may be filtered from the processed waste, compacted and disposed of in a conventional manner, whereas the waste liquids may be passed into the municipal sewer lines. As shown in FIG. 1, waste solids may be captured by a filtering device 32, while waste liquid may be discharged into the sanitary sewer system via pipe 34. The waste solids may then be disposed of as ordinary solid waste via a municipal trash compactor.

According to one embodiment, the processed waste may be filtered to separate solids in excess of a prescribed dimension to permit for drying of the solids by a suitable dehydration or drying apparatus. According to another embodiment, processed waste solids may be compacted by suitable compacting apparatus to further reduce waste volume.

Waste processing in the foregoing manner may be programmatically controlled in accordance with an operating system 26 or a pre-established system program. Variables such as pump speed, fluid flow rate, slurry ozone concentration, ozonated water temperature, and duration of operation may be selected within prescribed ranges in accordance with such factors as the nature and quantity of waste to be treated, and the concentration of ozone mixed in solution therewith. Further parameters which affect waste processing may include the dimensions of the conduits through which processed material and fluid flow. The foregoing variables and parameters may be selected to provide for the production of processed waste solids of a size in the range of from about 1/16 in. (1.5 mm) to about 1/4 in. (6.5 mm) in their largest dimension.

A printout of system operation parameters such as ozone concentration, exposure time and waste temperature throughout the processing procedure may optionally be provided to render a permanent record of system operation. Likewise, at the end of every sterilization cycle, a detailed sterilization report may be electronically printed by the operating system 26 illustrating, for example, the date, batch, time of start and finish of cycle. Alternatively, or in conjunction with printer operation, the various above-referenced operation various parameters may be stored in electronic memory for subsequent recall and display on a visually perceptible device such as a cathode ray tube (CRT) or similar display of alphanumeric and graphic data. In all instances, however, the waste processing proceeds for a period of time which provides for grinding and exposure of the waste to a circulating stream of ozonated water for a period of time that meets or exceeds the applicable standards and regulations governing material disinfection and sterilization in accordance with the selected form of waste treatment.

According to another embodiment, a housing 54 (See FIG. 4) may optionally be provided to enclose the OSS 100 and provide acoustic dampening.

Figure 2:
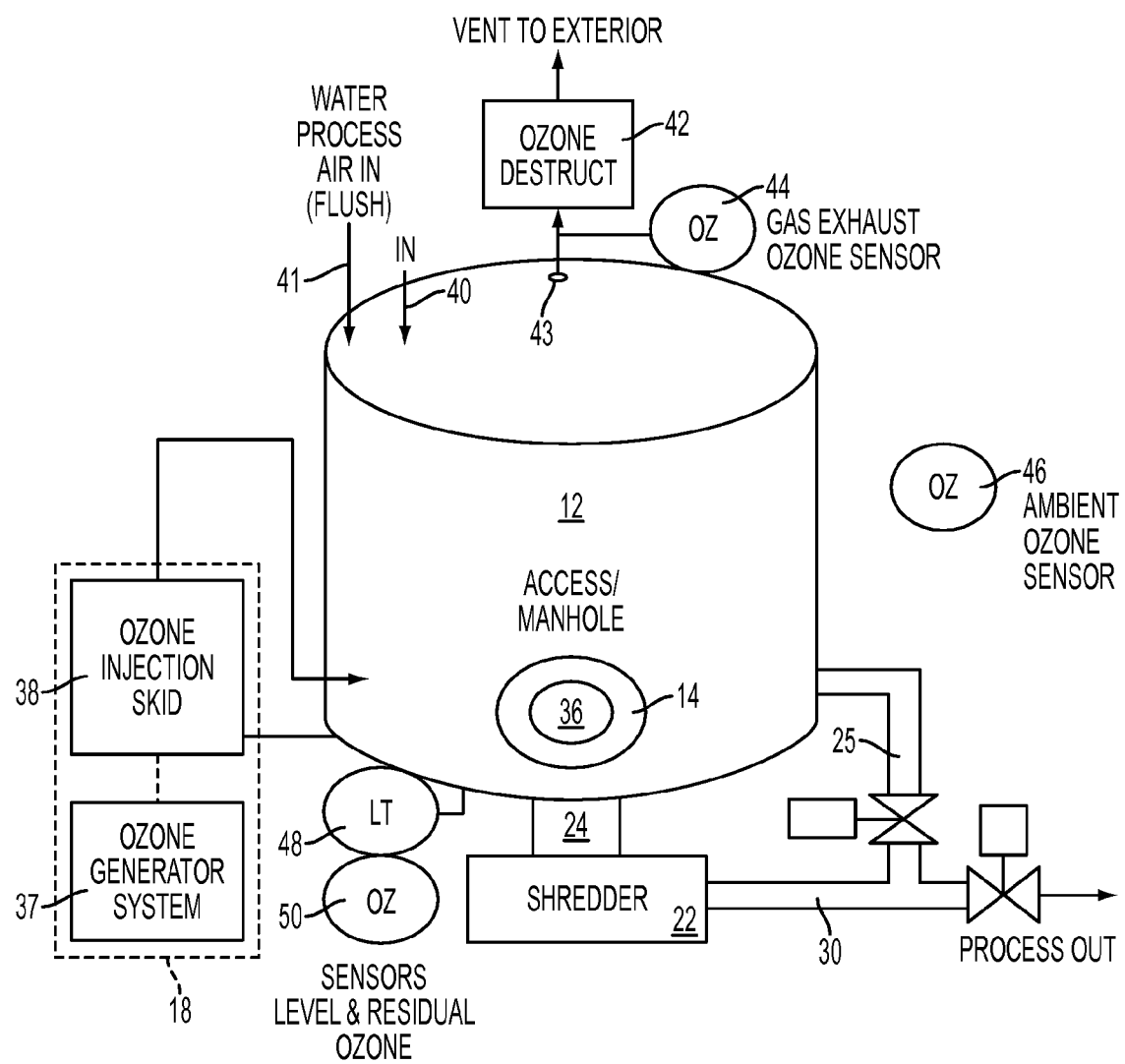
FIG. 2 is a perspective view of the process tank of the ozone sterilization system, in accordance with an embodiment of the present invention.

FIG. 2 is a perspective view of the process tank 12 of the OSS 100 in accordance with an embodiment of the present invention. The process tank 12 may include an access hole 36, having a lip (not shown) and an interior gasket 14, to be covered by door 16 during the ozonation and sterilization cycles.

The ozone system 18, in the embodiment of FIG. 2, may include an ozone generator 37 and an ozone injection skid 38. The ozone generator 37 may generate ozone gas, for example, in the manner described above. The ozone injection skid 38 may connect to the process tank 12 to "inject" ozonated water and/or ozone gas from the ozone generator 37 into the process tank 12.

The process tank 12 may include a water feed 40 and an air feed 41 to "flush" or clean the process tank 12 with air and/or water after the sterilization cycle is complete.

Additionally, the process tank 12 may include an air vent 43 to exhaust gas from the tank after use. A gas exhaust ozone sensor 44 may be connected to the air vent 43 to monitor the ozone concentration of the exhausted gas. If ozone levels are too high for release into the ambient air, an ozone destruct 42, connected to air vent 43, may filter the air through a charcoal filtering system to remove the excess ozone before exhausting the air into the ambient.

Ozone is a sharp irritant, and prolonged breathing of concentrations in excess of 1 ppmv should be avoided. The sharp odor of ozone is an indication of its presence. Ozone may be readily detected at concentrations of 0.1 ppmv or less (0.01 to 0.04 ppmv is the recognized odor detection threshold). The nose, however rapidly loses its ability to smell ozone. Odor alone should not be used as a warning of high ozone concentrations. Therefore, as shown in FIG. 2, an ambient ozone sensor 46 may be positioned in close proximity to the process tank 12 to detect and monitor the amount of ozone in the ambient air. This may serve as a safety feature to protect nearby users of the OSS 100.

Regarding the safety of ozone, gaseous ozone undergoes a thermal decomposition to oxygen at ordinary temperatures. This effect is accelerated by increases in temperature. For example, at 100° C., the half life of 5 wt. % ozone is 1.4 hours; at 300° C. the half life is 0.01 second. Commercial thermal ozone destruct units expose ozone to 350° C. for 4-5 sec. Mechanical interaction with solutions of ozone, e.g., those useful in accordance with embodiments of the present invention, will also decompose to oxygen. Further information may be found in a very comprehensive document prepared by the Compressed Gas Association, CGA P-34, Safe Handling of Ozone-containing Mixtures Including the Installation and Operation of Ozone-Generation Equipment. This document is available from the CGA at www.cganet.com.

Tank temperature and ozone sensors 48, 50 may be provided to monitor the temperature and ozone concentration levels of the slurry within process tank 12. If the ozone concentration level of the slurry is low, the operating system 26 may signal the ozone system 18 to inject additional ozone gas into the process tank 12.

Figure 3:
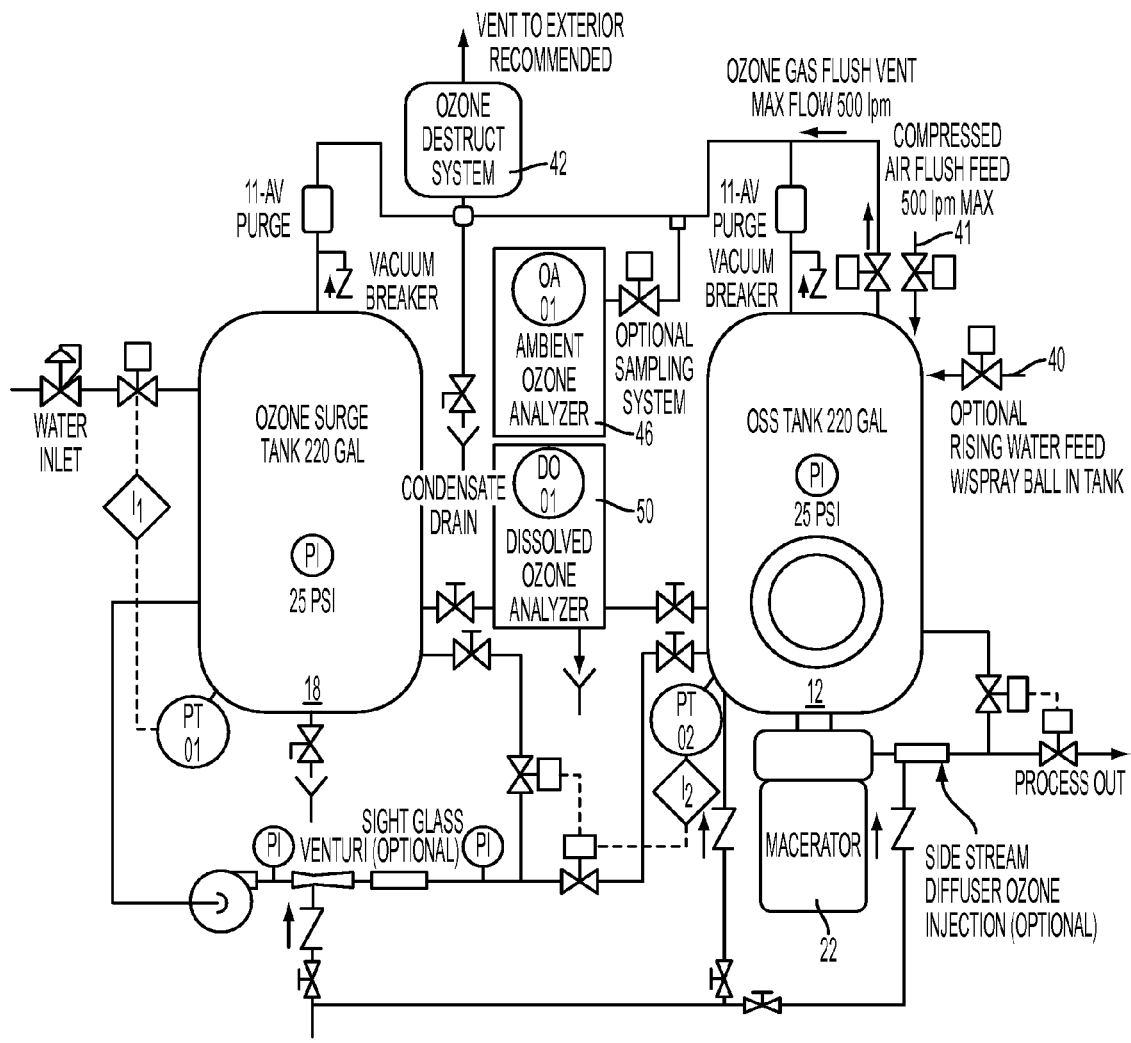
FIG. 3 is a system diagram of the process tank and the ozone system of the ozone sterilization system, in accordance with an embodiment of the present invention.

FIG. 3 is a system diagram of the process tank and the ozone system of the ozone sterilization system in accordance with an embodiment of the present invention and further exemplifies the features described above.

Figure 4:
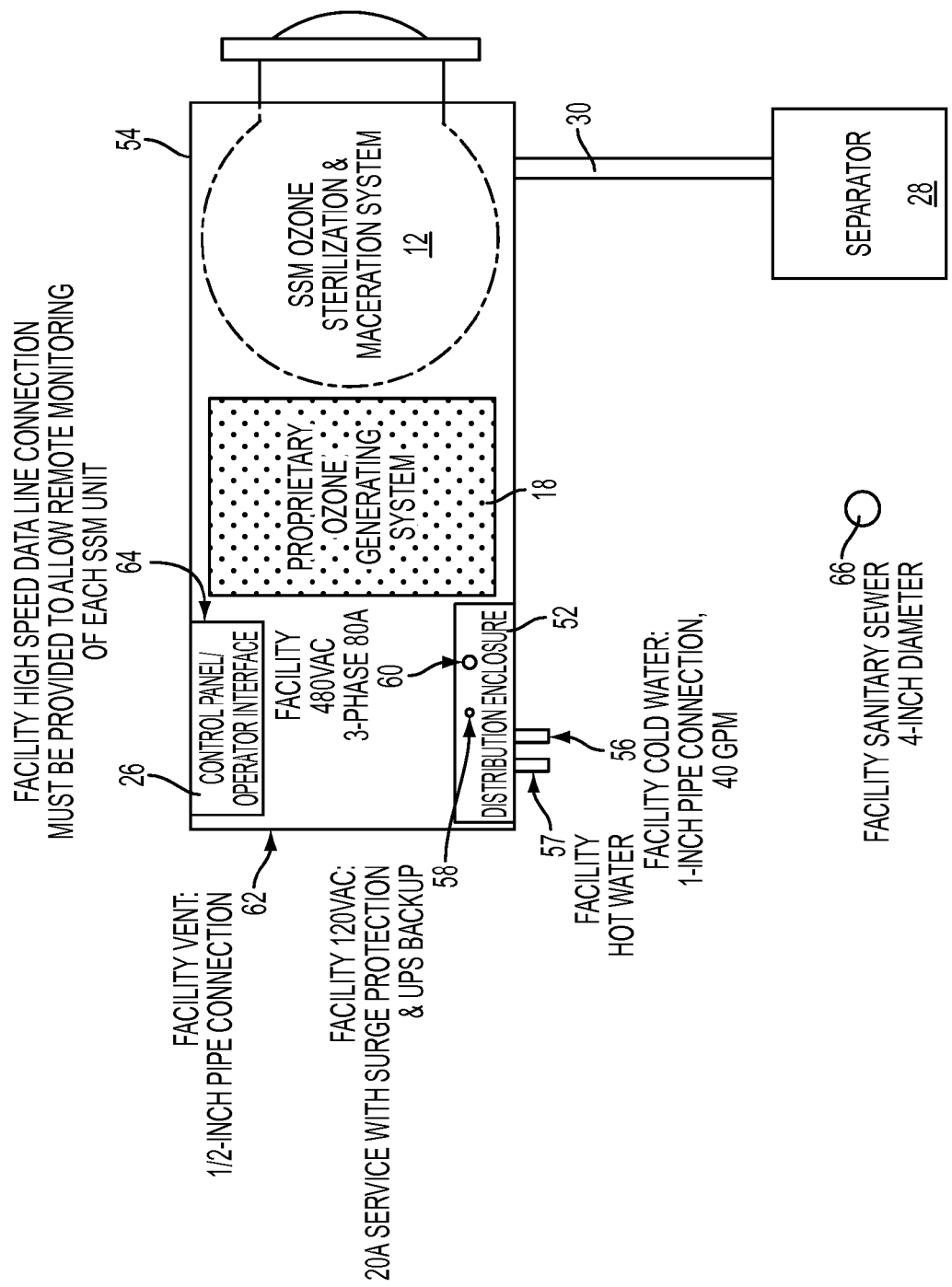
FIG. 4 is a schematic diagram showing the size and set up of the ozone sterilization system, in accordance with an embodiment of the present invention.
Figure 5A:
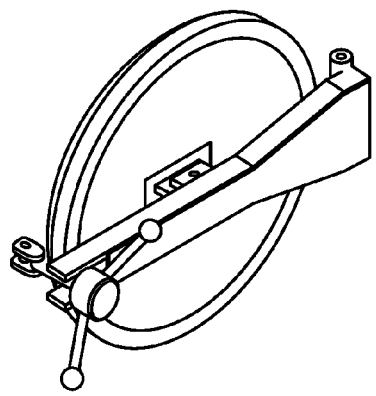
FIG. 5A-5E depict various perspective views of the door of the process tank of the ozone sterilization system, according to one embodiment of the invention.
Figure 5B:
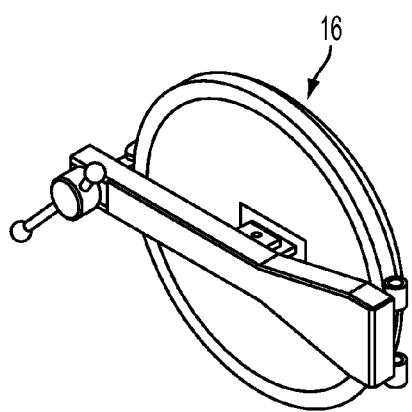
Figure 5C:
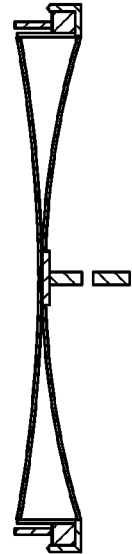
Figure 5D:
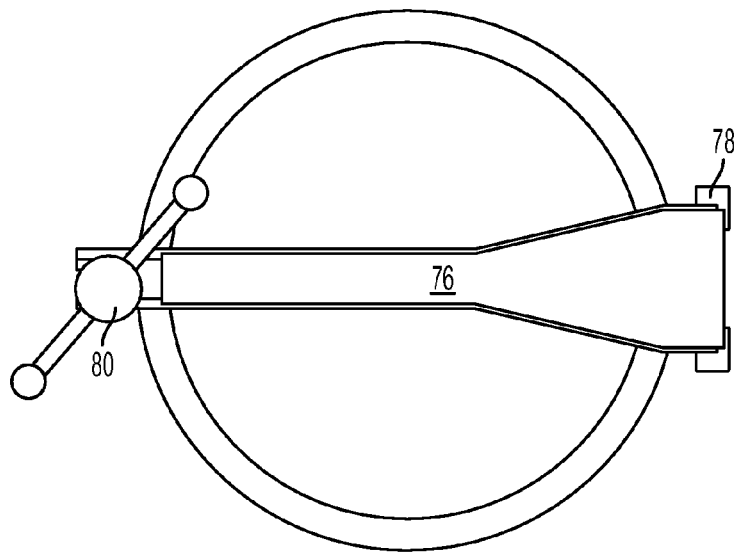
Figure 5E:
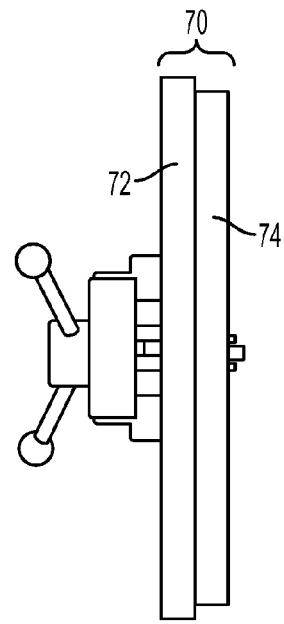

FIG. 4 is a schematic diagram showing the size and set up of the ozone sterilization system 100 in accordance with a different embodiment of the present invention. According to one embodiment, the OSS 100 may fit within a 46" by 116" rectangular foot print, with an external filter separator 28. Thus, the OSS 100 is compact and easily adapted to be placed in pre-existing building spaces.

The embodiment of FIG. 4 also shows a distribution enclosure 52 positioned within an overall housing 54 of the OSS 100. The distribution enclosure 52 includes a facility 120 Volt AC connection 58, and a facility 480 Volt AC connection 60. The facility cold water connection 56 that connects into housing 54 may supply, for example, water into the OSS 100 at approximately 40 gallons per minute and may be a 1-inch pipe connection. The facility hot water connection 57 that connects into housing 54 may supply, for example, water into the OSS 100 at approximately 10 gallons per minute at a temperature of approximately 120° F. to approximately 150° F. The facility hot water connection 57 may be a 3/4 inch pipe connection and may supply approximately 70 gallons of water into the OSS 100 two times per hour. The pressure requirements for both the facility cold and hot water connections 56, 57 may be between about 40 psi to about 60 psi. The facility 120 Volt AC connection 58 may, for example, be a 20 Amp service with surge protection and UPS backup. The facility 480 Volt AC connection 60 may, for example, be a three-phase 80 Amp service. The housing 54 of the OSS 100 may further include a facility vent 62 having, for example, a half inch pipe connection.

According to the embodiment shown in FIG. 4, the operating system 26, also referred to as the "Control Panel/

Operating Interface," may include a facility high speed data line connection 64 to allow remote monitoring of each OSS 100 unit in the facility. FIG. 4 shows the location and proximity of a facility sanitary sewer line 66 from the filter separator 28. The facility sanitary sewer line 66 may have, for example, a four-inch diameter.

FIG. 5A-5F show various views of the door 16 of the process tank 12 of the ozone sterilization system 100 according to one embodiment of the invention. The door 16 includes a door body 70 having an exterior plate 72 of sufficient size to securely cover the outside of the access hole 36 (See FIG. 2) and a smaller interior plate 74 adapted to engage the gasket 14 of the access hole 36 to preserve an air-tight seal of the process tank 12 while the door 16 is closed during sterilization. As shown in the cross-sectional view of FIG. 5C, the door body 70 of the door 16 may be concave to provide a greater resistance to the pressure within the process tank 12. The curvature of the door body 70 allows the door 16 to withstand greater pressure per square inch.

The door 16 further includes a structural lever 76 that is connected to and spans across the width of the exterior plate 72 and is hingedly attached via a hinge device 78 to the exterior housing of the process tank 12. On an opposite side of the hinge device 78, the structural lever 76 connects to a door latch 80 that may be twisted or turned to tighten the door 16 in an air-tight seal. Additionally, the operating system 26 may include a door sensor (not shown) to alert a user if the door is open or unlocked.

According to one embodiment, the access hole 36 and the door 16 are substantially circular in shape. Other shapes may be used as well. According to another embodiment, the access hole 36 of the process tank 12 may be sufficiently sized to receive at least one 32 to 34 gallon-sized bag of RMW 10. For example, an interior diameter of the access hole 36 may be approximately 24 inches. The access hole 36 may further be sufficiently positioned to allow an operator to easily place the RMW 10 into the process tank 12.

Figure 6:
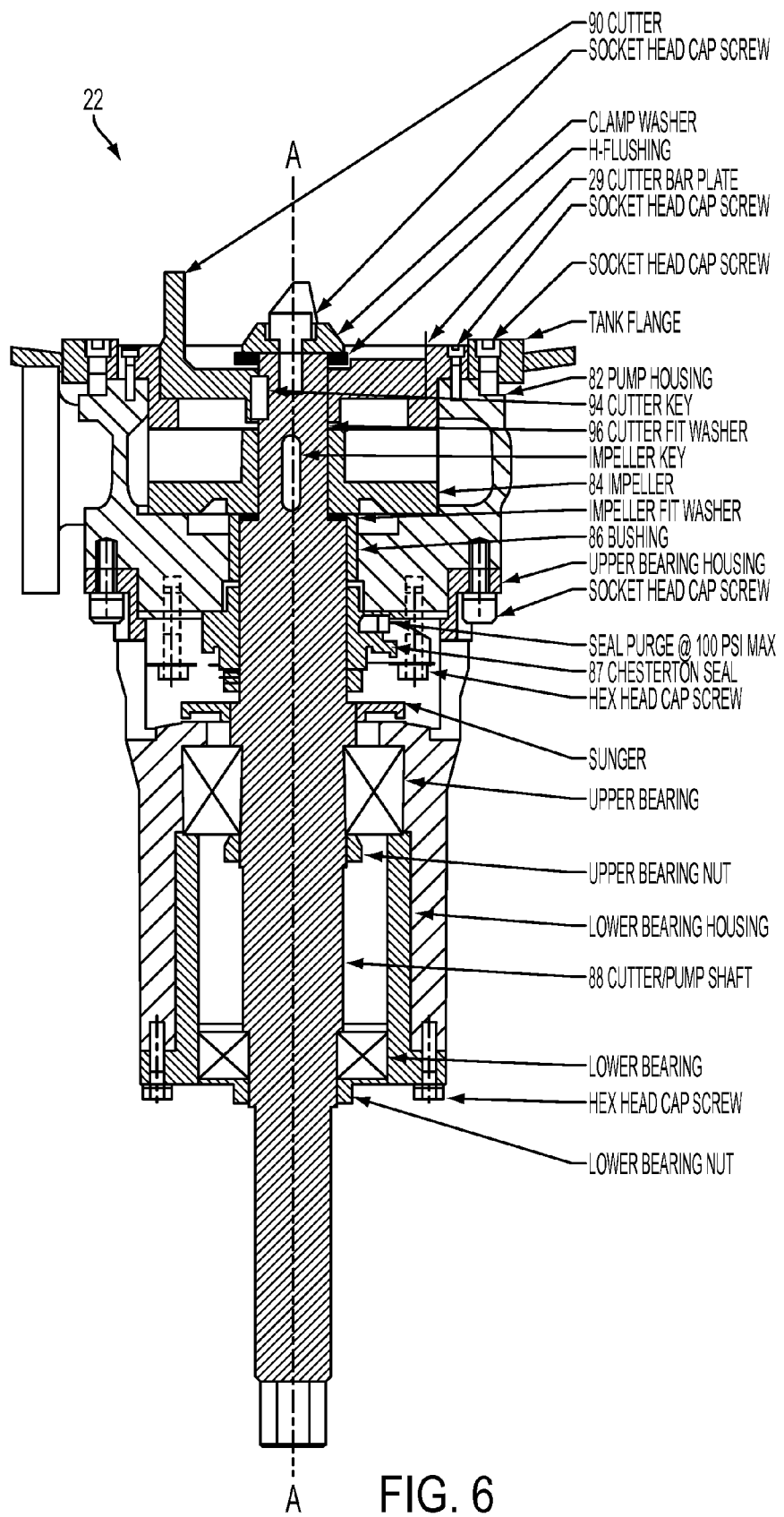
FIG. 6 is a cross-sectional view of the cartridge/cartridge/macerator pump of the ozone sterilization system, according to an embodiment of the present invention.

FIG. 6 is a cross-sectional view of the cartridge/cartridge/macerator pump 22 of the ozone sterilization system 100 according to an embodiment of the present invention. The cartridge/cartridge/macerator pump 22 includes a cutter/pump shaft 88 aligned along an axis A and a surrounding pump housing 82. The cartridge/cartridge/macerator pump 22 may function as both a pump assembly and a cutter/chopper assembly. The pump assembly of cartridge/cartridge/macerator pump 22 may include an impeller 84 and a bushing 86 driven by the cutter/pump shaft 88. The cartridge/macerator pump 22 may further include a seal 87, for example, but not limited to a Chesterton seal. The cutting/chopping assembly of cartridge/macerator pump 22 may include a cutter 90, a cutter bar plate 92, a cutter key 94 and a cutter fit washer 96, also driven by the cutter/pump shaft 88, to reduce the size of the RMW 10 particles.

As shown below (See FIGS. 11A-11E), the cartridge/macerator pump 22 is positioned beneath the bottom of process tank 12. The slurry may be drawn into the pump 22 via impeller 84. The slurry may be first chopped by cutter 90, which may be a single-blade assembly that rotates within the process tank 12. The slurry may then be further reduced in size by the cutter bar plate 92, which may be a circular disk that includes a plurality of cutting surfaces positioned along an inside perimeter surface. The cutter bar plate 92 may be positioned between cutter 90 and impeller 84. This stacked configuration is known as a "cartridge system." The impeller 84 itself may include a plurality of cutting surfaces that may further reduce the size of the slurry particles. Once, the slurry has passed through the cutter 90, the cutter bar plate 92 and the impeller 84, it may be re-circulated back into process tank 12 for additional ozonation and chopping.

Figure 7A:
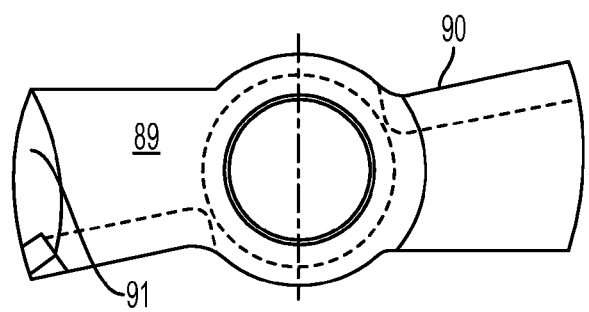
FIGS. 7A-7C are various views of the cutter of the cartridge/cartridge/macerator pump of the ozone sterilization system, according to an embodiment of the present invention.
Figure 7B:
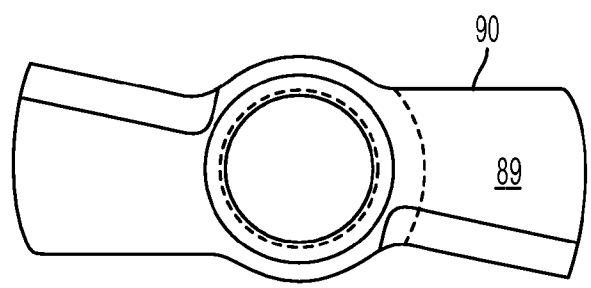
Figure 7C:
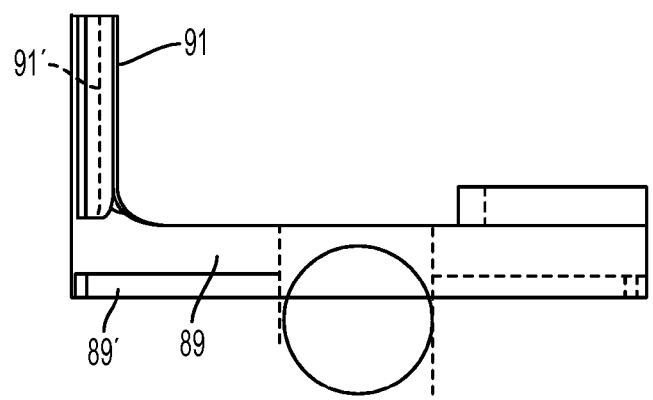
Figure 8A:
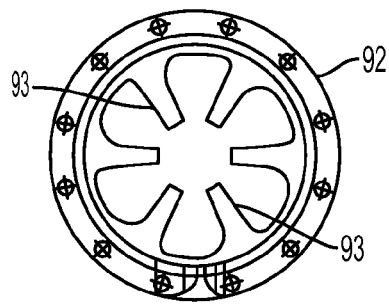
FIGS. 8A-8D are various views of the cutter bar plate of the mascerator pump of the ozone sterilization system, according to an embodiment of the present invention.
Figure 8B:
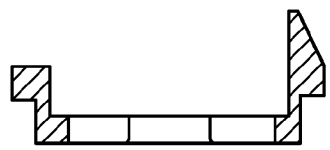
Figure 8C:
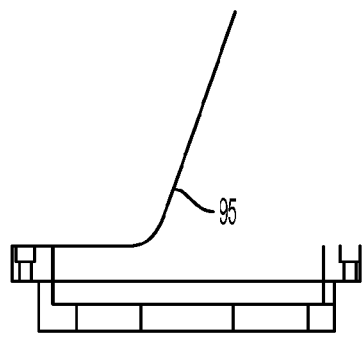
Figure 8D:
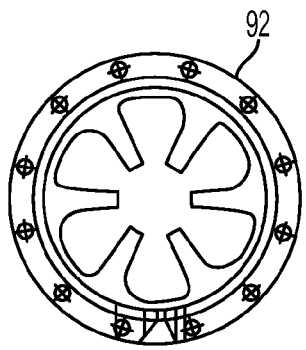

FIGS. 7A-7C are various views of the cutter 90 of the cartridge/macerator pump 22 of the ozone sterilization system 100, according to an embodiment of the present invention. The cutter 90 may include a base portion 89 and a blade portion 91 that projects upwards into the process tank 12 at a substantially perpendicular angle at one end of the base portion 89. The base portion 89 may span horizontally across and parallel above the impeller 84. The base portion 89 may include a carbon insert 89' along a bottom edge. The carbon insert 89' may be positioned beneath blade portion 91 to provide extra strength and durability during maceration. The blade portion 91 may also include a carbon insert 91', which may provide extra strength and durability of the blade portion 91 during cutting, such as chopping, of the slurry. According to one embodiment, the cutter 90 may made of a brazed carbide material. According to another embodiment, the cutter 90 may be a double-sail cutter.

FIGS. 8A-8D are various detailed views of the cutter bar plate 92 of the cartridge/macerator pump 22 of the ozone sterilization system 100, according to an embodiment of the invention. The cutter bar plate 92 may be a circular plate having a substantially hollow center. The interior portions of the cutter bar plate 92 may include a plurality of cutting surfaces 93. As the slurry is drawn through the hollow center of the rotating cutter bar plate 92 during maceration, the cutting surfaces 93 contact and further reduce the size of the slurry particles. Additionally, the cutter bar plate 92 may include a projection 95 that may be used to dislodge waste debris that become stuck above in the cutter 90.

Figure 9:
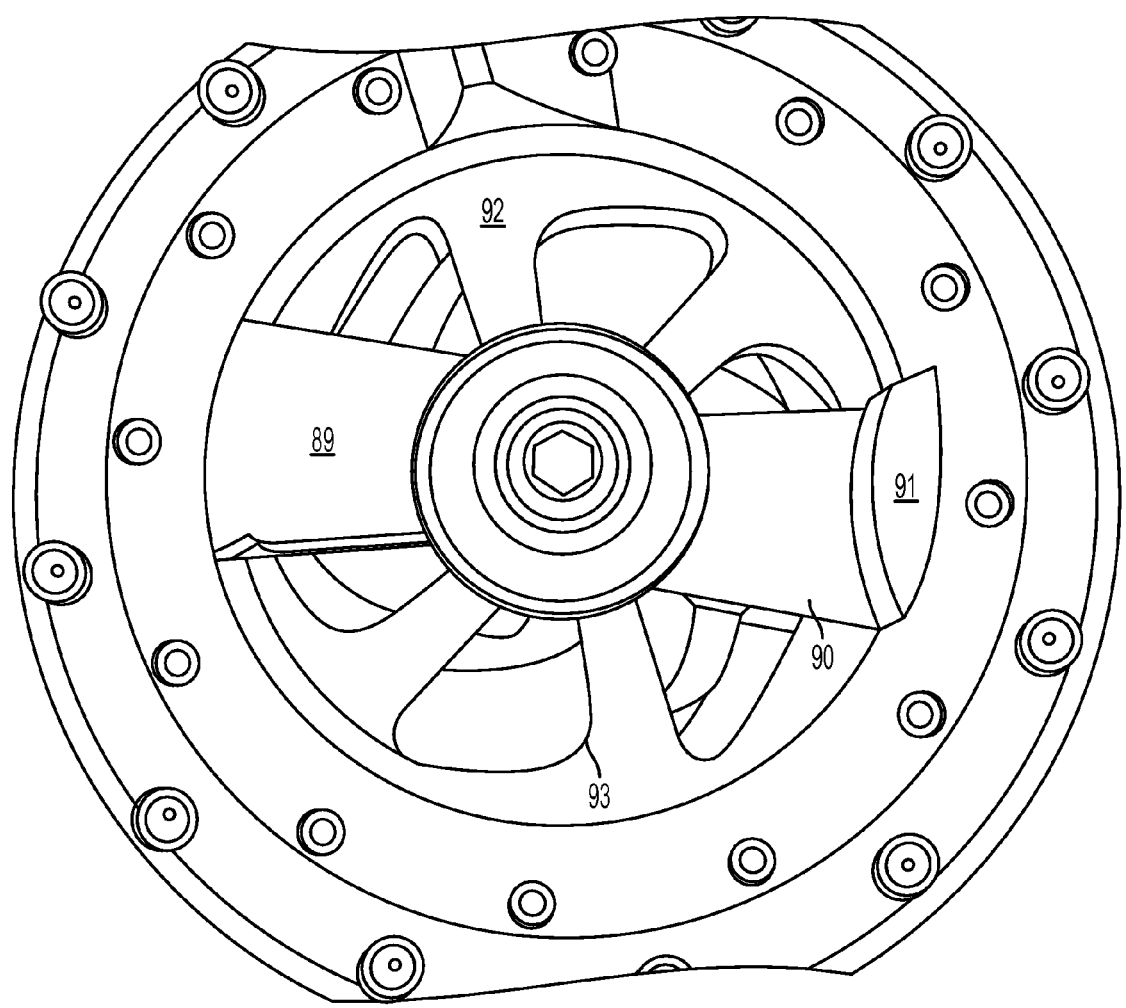
FIG. 9 is a front view of the cutter portion of the cartridge/cartridge/macerator pump, according to an embodiment of the invention.
Figure 10:
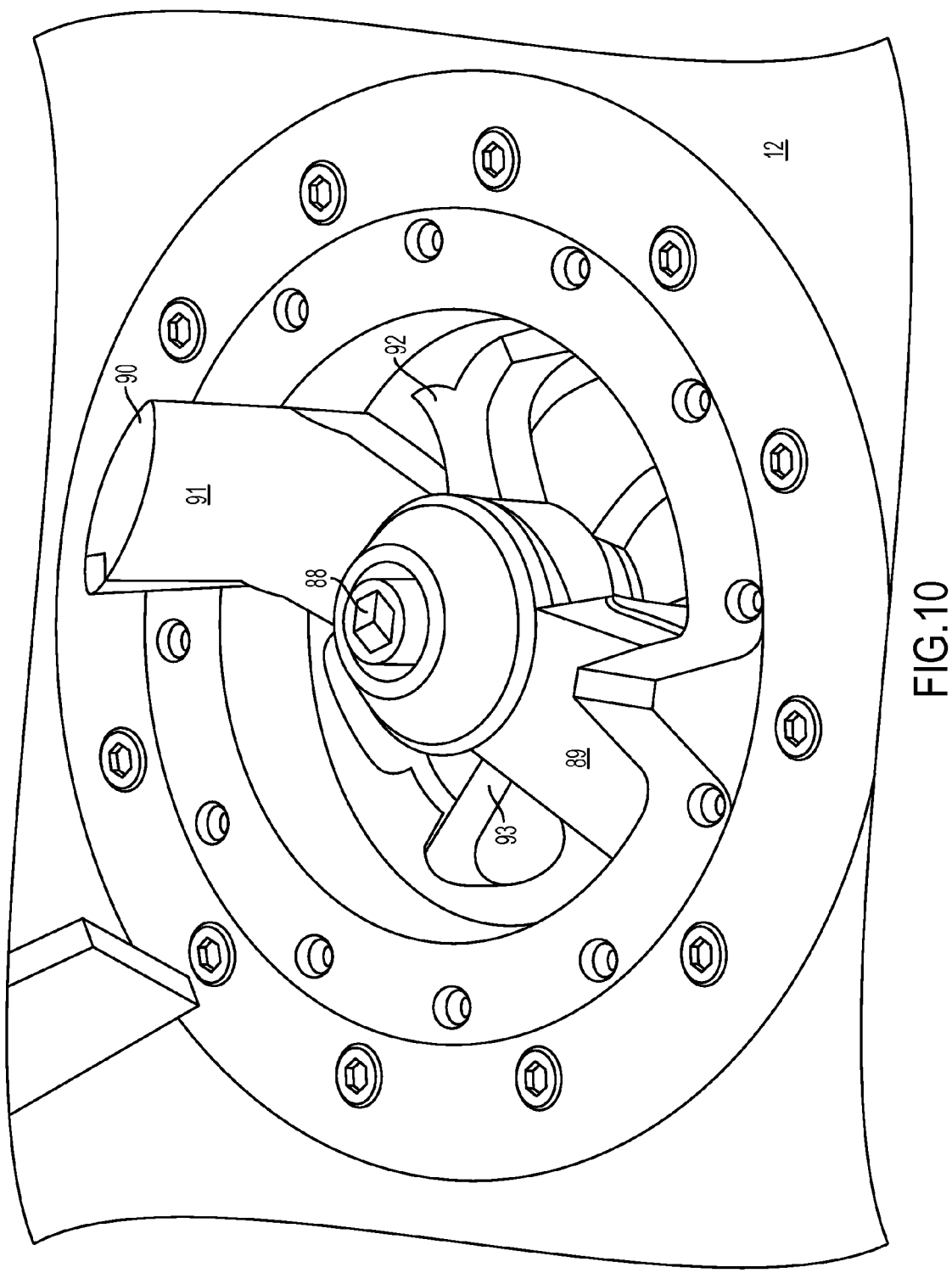
FIG. 10 is a front view of the cutter portion of the cartridge/cartridge/macerator pump assembled within the process tank, according to an embodiment of the present invention.

FIG. 9 is a front view of the cutter portion of the cartridge/macerator pump 22, according to an embodiment of the invention. FIG. 10 is a front view of the cutter portion of the cartridge/macerator pump 22 assembled within the process tank 12, according to an embodiment of the present invention.

Figure 11B:
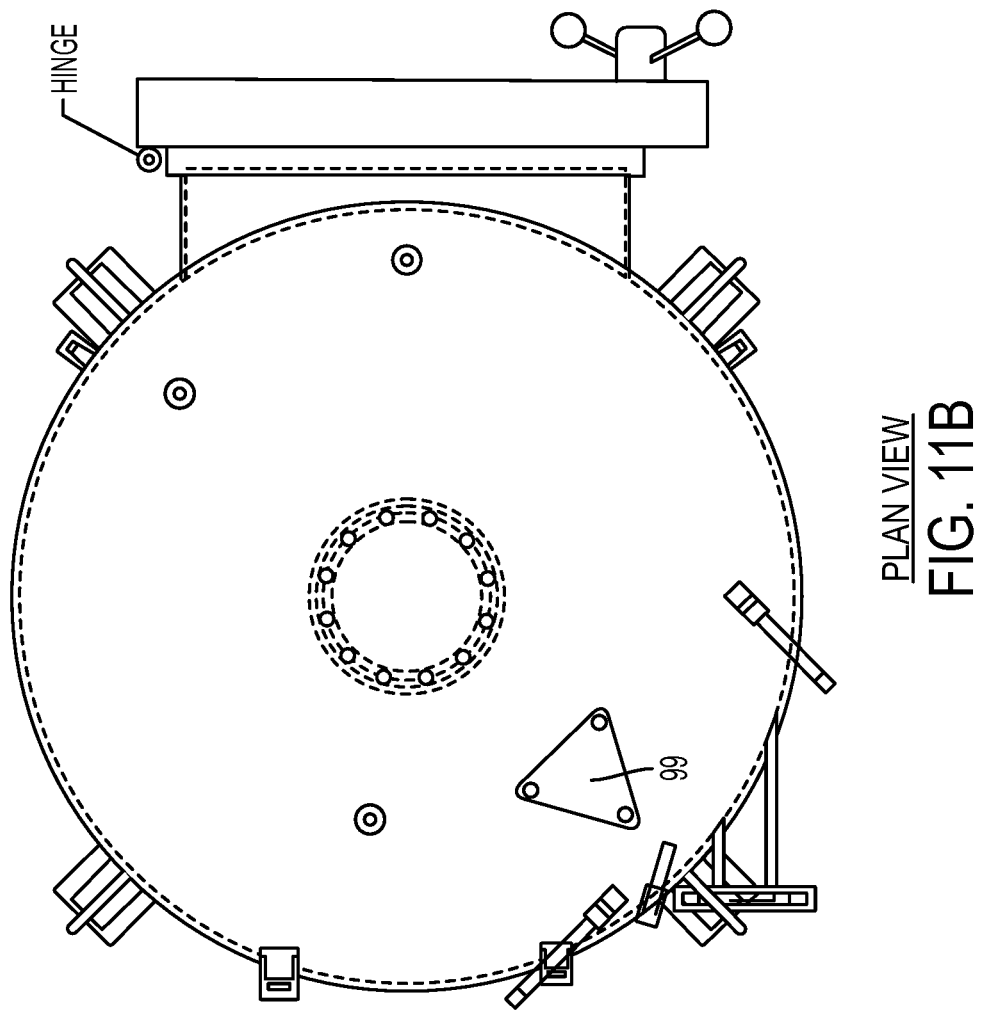
Figure 11C:
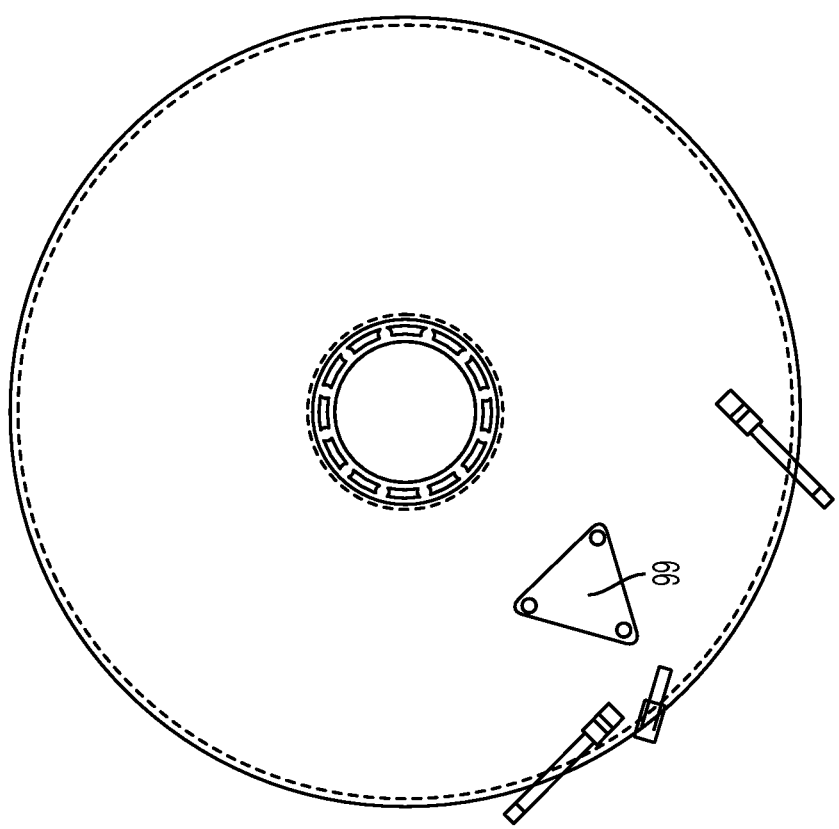
Figure 11D:
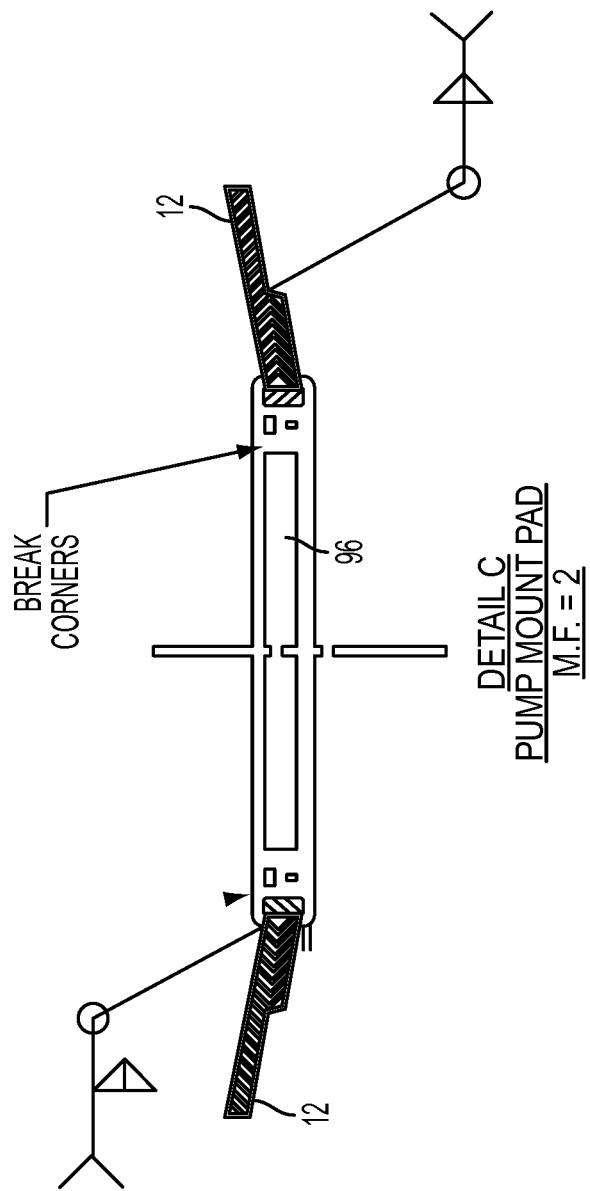

FIGS. 11A-11E depict various views showing the connection of the cartridge/macerator pump 22 to the process tank 12, according to an embodiment of the invention. FIG. 11A shows an elevational view of the process tank 12. In this embodiment, a pump mounting pad 96 may be positioned in the center bottom surface of the process tank 12 for connection with the cartridge system of the cartridge/macerator pump 22. A detail of the pump mounting pad 96 is shown in FIG. 11D. According to one embodiment, the pump mounting pad 96 may have an outer diameter of approximately 10.5 inches and an inner diameter of approximately 9.5 inches. According to another embodiment, the cartridge/macerator pump 22 is mounted to the bottom of the pump mounting pad 96. The position of the pump mounting pad 96 may allow the slurry to be easily drawn into the cartridge/macerator pump 22.

Figure 11E:
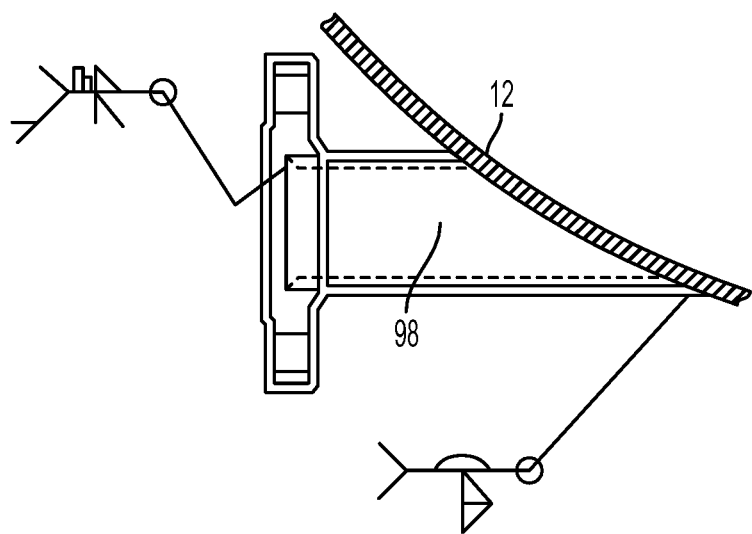

A recirculation connection 98 may be positioned in a side wall or shell of the process tank 12. The recirculation connection 98 may be connected to the recirculation loop 25 downstream of the cartridge/macerator pump 22. The recirculation connection 98 may be centered in height along the vertical wall of the process tank 12 or slightly below center. The recirculation connection 98 may be positioned slightly off-center from the door 16. The positioning of the recirculation connection 98 may allow the slurry to drop down into the process tank 12 towards the pump mounting pad 96 and, thus, into the cartridge/macerator pump 22. A detail of the recirculation connection 98 is shown in FIG. 11E.

A deflector mounting plate 99 may be mounted to the bottom surface of the process tank 12 to push or deflect the re-circulated slurry or debris back into the cartridge/macerator pump 22. In one embodiment, the deflector mounting plate 99 may be positioned substantially below the recirculation connection 98 to receive the re-circulated slurry returning into the process tank 12. In another embodiment, the deflector mounting plate 99 may be tilted or otherwise arranged to deflect a pre-determined amount of slurry back into the cartridge/macerator pump 22. The approximate positioning of the deflector mounting plate is shown in FIGS. 11B and 11C.

According to another embodiment, the OSS 100 may follow one or more of the following method steps to initialize and carry out the ozone sterilization of the RMW 10: 1) "Ready-to-Start," the bags of waste material are loaded into the process tank and ready for the door to be closed and the machine started; 2) "Ozonate," ozone and water is recirculated in the process tank; 3) "Grind, Recirculate, and Sterilize," the waste material is ground and recirculated with ozone until the waste debris are sterilized; 4) "Cool Down and Discharge," the ground and sterilized waste is cooled down with fresh water and discharged into the filter separator; "Drain and Dispose," water from the cooled process is drained in a sanitary sewer, while unrecognizable, sterile remains are ready for disposal in regular trash; and "Confirmation," a computer prints a receipt verifying the process and stores results in a history record.

Figure 12:
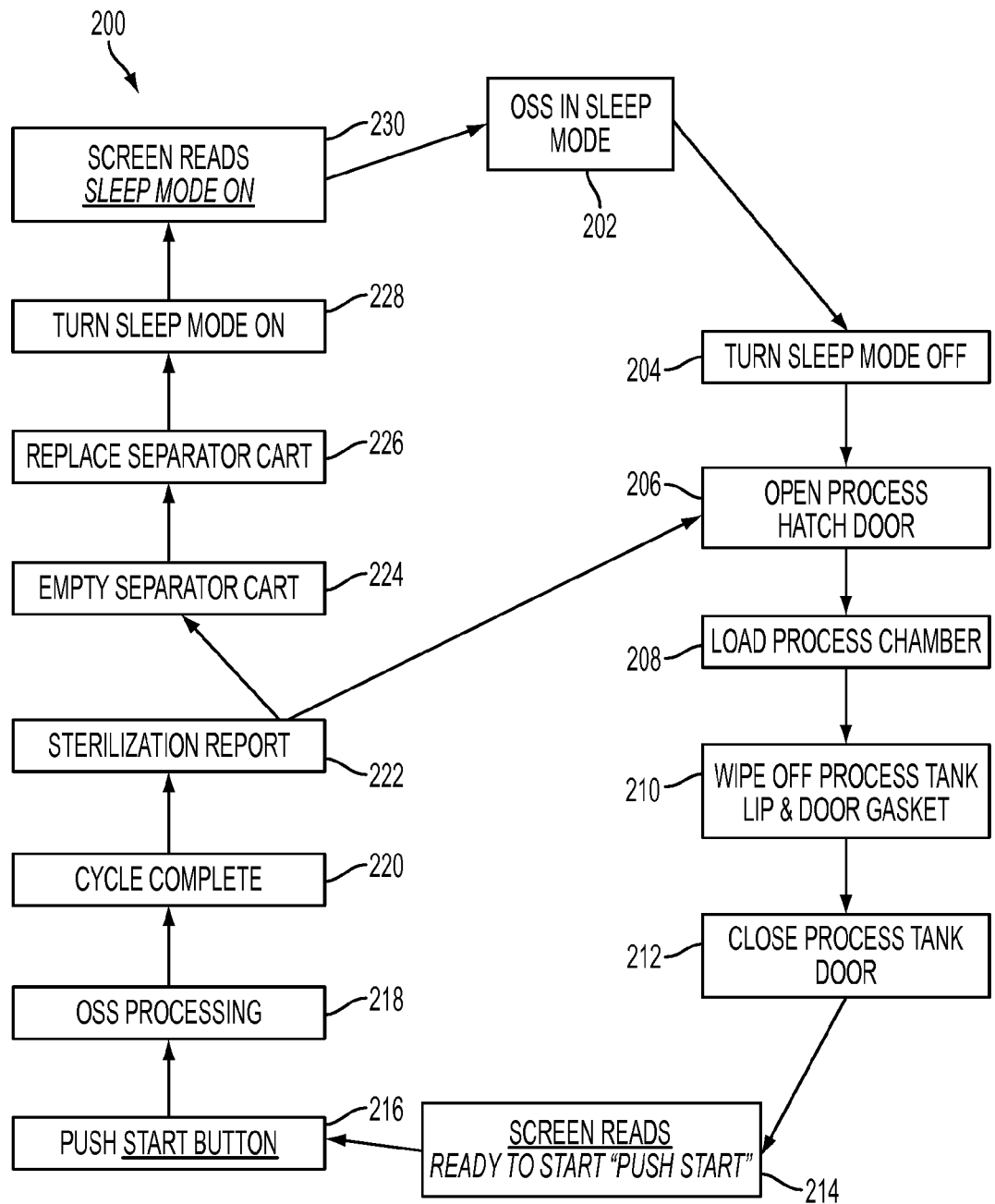
FIG. 12 is a block diagram of the operations method of the ozone sterilization system according to an embodiment of the present invention.

FIG. 12 is a block diagram of the operation method 200 of the ozone sterilization system 100 according to one embodiment of the present invention. In this embodiment, the OSS 100 may begin in sleep mode 202. After turning the sleep mode off 204, an operator may open the process hatch door 206, load the process tank 208, wipe off the process tank lip and door gasket 210 and close the process tank door 212. A display screen of the operations system 26 may read "Ready for start: PUSH START" 214. The operator may then push the start button 216, wherein the operations system 26 may start OSS processing 218. Once the sterilization cycle is complete 220, the operations system 26 may compile and produce a sterilization report 222. The operations system 26 may signal the operator to open the process tank door 206 and empty the separator cart 224. The operator may then replace the separator cart 226 and the operations system 26 may return to sleep mode 228. During sleep mode 228, the display screen may read "Sleep mode ON" 230.

According to another embodiment, during start-up of the OSS 100, an operator may use the operating system 26 to confirm that all of the system parameters are prepared properly on a screen display. The start parameters may include an ozone system check, a check of various safety features, including, but not limited to, that the process tank door 16 is closed and secured, a cold water temperature sensor check, and an electricity check. Once these start parameters have been satisfied, a start button may be pressed, and operation of the OSS 100 may be engaged.

According to one embodiment, there may be no further human operator intervention in the process after the start button is pressed until the sterilization cycle is completed. According to another embodiment, the operator may be required to move away from the immediate vicinity of the OSS 100.

FIG. 13 is a chart 300 showing control stages of the ozone sterilization system according to an embodiment of the present invention. In this embodiment, the initial stage 302 initializes the ozone generator to produce ozonated water. In the sleep stage 304 the unit remains locked so that it cannot be started. The sleep stage 304 recovers to the initial stage 302. In the ready-to-start stage 306 the unit is made ready for the process tank door to be closed and the start button to be pushed. The ready-to-start stage 306 recovers to the initial stage 302. The ozonate stage 308 fills the process tank with the ozonated water and ozone gas. The fill stage 310 fills the process tank with ozonated water. The grind stage 312 chops and recirculates the waste and the ozonated water through the process tank. The sterilize stage 314 calculates the sterilization time based on the ozone concentration and the time as material continues to be circulated. The venting stage 316 vents air from the process tank to the atmosphere. The discharge stage 318 discharges the contents of the process tank into the separator. The rinse stage 320 rinses the process tank with water from the facility. The drain stage 322 drains the process tank and the filter separator. The complete stage 324 prints a report and stores a history of the sterilization process.

The principles of the invention may be applied to the treatment of water soluble polymeric or fibrous waste materials, whereby treatment results in the dissolution of the waste material. The system may be used without any changes to achieve the dissolution of this waste material, as opposed to biological neutralization. In operation, the waste to be processed may be water soluble polymeric or fibrous waste material. Circulation within the closed waste processing system results in the dissolution of the waste material. Water dissolvable materials dissolve below boiling temperature. Thus, processing temperatures for dissolving the water soluble polymeric or fibrous waste material range from about 85° F. to about 165° F. Since temperatures below the boiling point of water are used, the treatment may be performed at lower pressure. A suitable pressure range may be, for example, from about 5 to about 25 PSI. The circuit components of the system for this specific use are formed from suitable materials that are capable of withstanding the temperature, pressure and abrasion associated with the operation of the waste processing system for treating water soluble polymeric or fibrous waste material. Since lower temperatures and pressures are used in this embodiment as opposed to biological neutralization, different kinds of material, known to a skilled artisan, may be used for the circuit components than are used for biological neutralization. The treatment of the water soluble polymeric or fibrous waste material according to the present invention results in the dissolution of the material. The processed liquid may be discharged into, for example, a municipal sewer system.

Ozone concentrations of from 5% to about 50% are used in accordance with embodiments of the present invention. Of course, the particular levels of ozone to be used in the systems and methods according to embodiments of the present invention may depend upon the amount of time the waste slurry is exposed to the ozone.

The ozone sterilization system has many advantages over the prior art. The ozone sterilization system, for example, is a process that uses a single process tank to sterilize waste material, rather than a batch processing system that uses multiple processing tanks. Thus, the OSS is compact and more efficient. The OSS may allow for the recovery of recyclable materials in separate batches. The OSS may treat both solids and liquids together or separately. The OSS may destroy HIPAA and classified paper documents. The OSS may also treat bio-waste laboratory materials, including blood and urine products.

While aspects of the above embodiments use ozone sterilization as part of a waste treatment system, embodiments of the current invention as not limited thereto. For example, embodiments of the current invention may include waste processing systems discussed below, with or without ozone sterilization.

Figure 14:
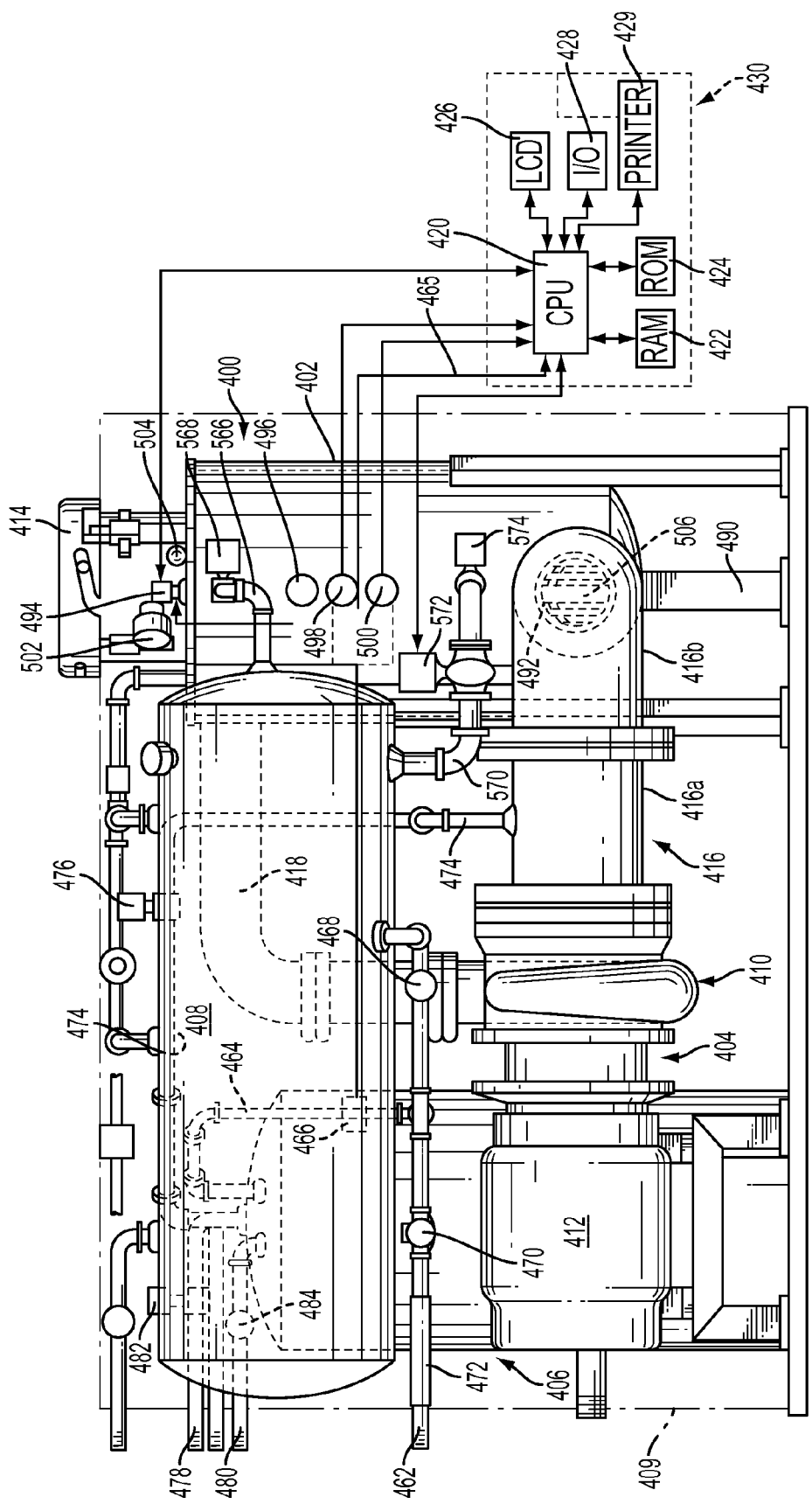
FIG. 14 is a side view of a waste processing according to an embodiment of the present invention.
Figure 15:
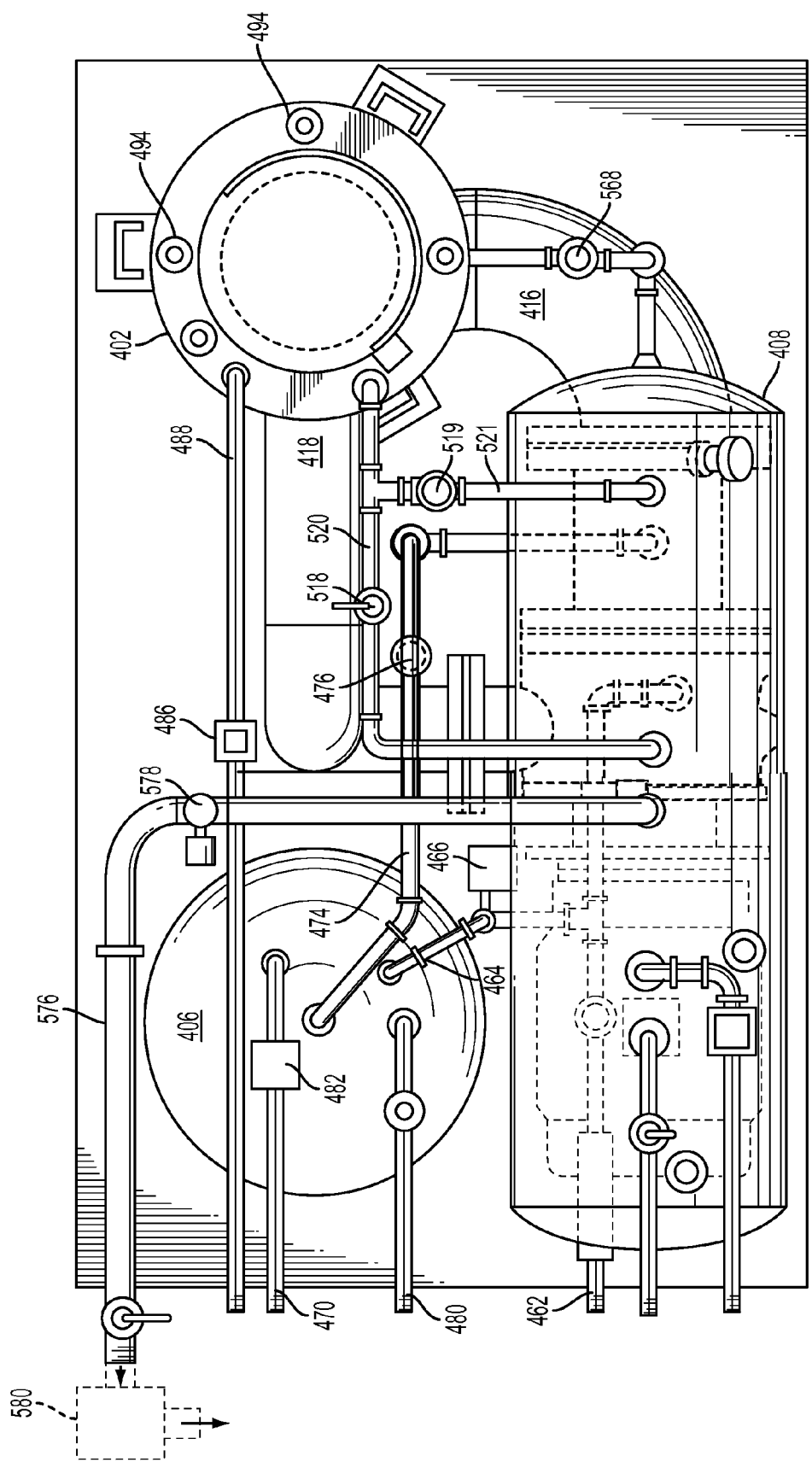
FIG. 15 is a top view of the apparatus depicted in FIG. 14.
Figure 16:
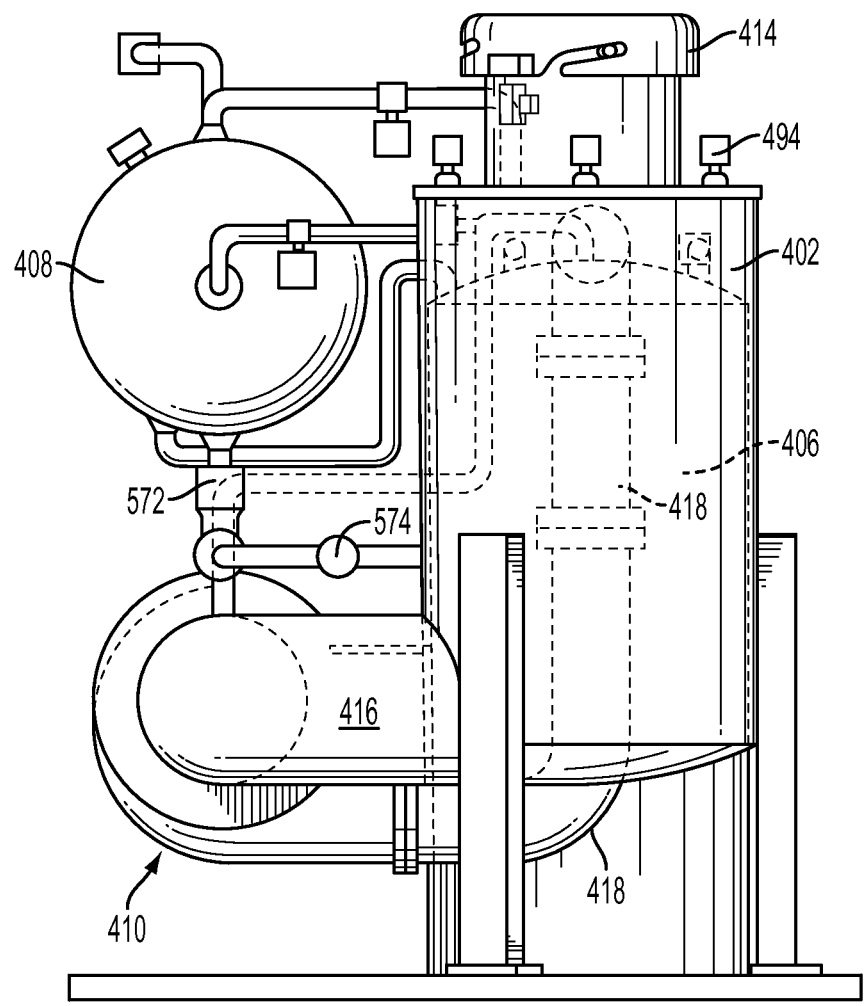
FIG. 16 is an end view of the apparatus depicted in FIG. 14.

According to another embodiment of the present invention, and with particular reference to FIGS. 14-16, there is depicted a waste processing system, designated generally by reference character 400. The system 400 is comprised generally of a decontamination chamber 402, a waste processing chopper/pump assembly 404 ("chopper pump"), a fluid reservoir 406 for heating and storing a fluid such as water to be mixed with the waste to be processed, and a cooling tank 408 for receiving waste processed by the system and for cooling it prior to disposal. A housing 409 can optionally be provided to enclose the system and provide acoustic dampening. The chopper/pump 404 is generally comprised of a grinder assembly 410 and a motor assembly 412 for providing power to the grinder assembly. A removable cover 414 is provided over an inlet 415 of the decontamination chamber 402 to permit user access to the interior of the chamber for depositing waste to be treated by the processing system 400. The waste can be in the form of virtually any type of non-toxic inorganic or organic material, such as medical waste, food waste, rubber, plastics, and the like for which it is desirable to disinfect, or optimally render biologically neutral (i.e., biologically inert or devoid of living organisms) via sterilization. Medical waste can include, by way of non-limiting example, sharps such as needles, knives and blades, trocars, clamps, glass containers, gauze and bandages, surgical gloves and gowns, and various other instruments and paraphernalia which contacts internal body fluids such as blood, lymphatics, semen and vaginal fluids. Waste sterilization is preferred in instances such as with some forms of medical waste where bacteria, viruses and/or spores may be present, in which case all living organisms associated with the waste must be destroyed prior to its disposal.

The invention is particularly useful for effecting sterilization of virtually all forms of non-toxic waste by exposing the waste to superheated water at a temperature in the vicinity of from about 270° F. (132° C.) to about 275° F. (135° C.) at a pressure of from about 55 psi to about 65 psi, thereby assuring that the fluid is maintained substantially in a liquid state. Waste treatment with superheated liquid water as opposed to water vapor is preferred due to its greater ability to intermix with the waste solids as they are ground and circulated by the chopper/pump 404. As will be described in considerably greater detail below, waste processing is accomplished by way of a closed, pressurized circuit which includes the decontamination chamber 402, pump 404, chopper/pump inlet conduit 416, grinder assembly 410, and the pump outlet conduit 418 extending between the pump and the decontamination chamber. Accordingly, each of the circuit components is formed from suitable materials that are capable of withstanding the extremes of temperature, pressure and abrasion that are associated with operation of the waste processing system of the present invention.

The various aspects of system operation (i.e., temperature, pressure, material flow control and the like) are controlled by a control processor (CPU) 420. A random access memory (RAM) 422 is electrically connected to the CPU 420 and stores OSS (Operation System Software) software and provides working memory to the CPU. A read-only memory (ROM) 424 is also provided which stores various programs that are needed for input/output, power-up, self-test diagnostics, and the like for the CPU. A display 426 such as a liquid crystal (LCD), light emitting diode (LED) or cathode ray tube (CRT) display that is operable to provide human intelligible signal output to a system operator can optionally be provided. Various input/output (I/O) means 428 such as keyboards, switches and the like are preferably provided to permit user input to the CPU. A printer 429 can optionally be connected to the CPU 420 to provide a printout of various data associated with operation of the waste processing system 400. All of the foregoing electronic components (CPU, I/O and the like) are preferably provided at a system control panel 430 that is readily accessible to the system user.

Figure 17:
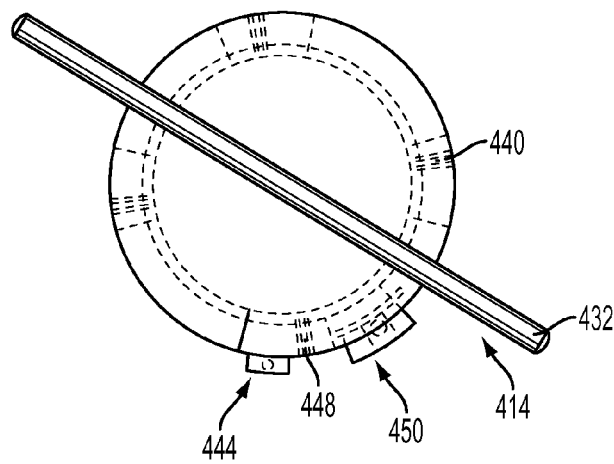
FIG. 17 is a top view of the waste decontamination chamber cover according to an embodiment of the present invention.
Figure 18:
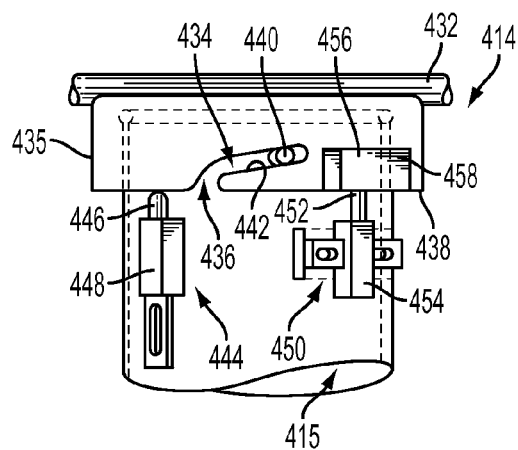
FIG. 18 is a side view of the cover and related cover locking hardware according to an embodiment of the present invention.

Waste material to be processed by the system is deposited in the decontamination chamber through the chamber inlet 415. As the waste material and water is to be exposed to relatively high pressure, the cover 414 is configured so as to withstand these pressures and to prevent inadvertent opening during the course of system operation. Details of the cover construction are depicted in FIGS. 17 and 18. An oversized handle 432 is provided which extends across the cover to facilitate user manipulation of the cover to attain the requisite level of decontamination chamber sealing. A slot 434 is provided at four equidistantly-spaced positions along the side 435 of the cover. Each slot 434 extends away from a slot opening 436 at the rim 438 of the cover in a direction that is counter to the direction of cover rotation to effect sealing of the decontamination chamber 402. The slots 434 are dimensioned to receive therein a corresponding key 440 which extends radially outwardly from the decontamination chamber outer surface adjacent to its inlet 415. Due to the rearward inclination of the slot 434, as the cover is rotated clockwise (i.e., toward a locked position in the depicted embodiment), each slot follows its correspondingly received key 440, resulting in a downward exertion of pressure by the key 440 against the lower surface 442 of its corresponding slot.

A sensor 444 (FIG. 18) is provided along the chamber exterior adjacent to one of the keys 440. The sensor includes a plunger 446 that is reciprocably extensible with respect to a sensor housing 448. Biasing means such as a spring (not shown) received within the sensor housing 448 biases the plunger 446 outward from the housing 448 and into engagement with the cover rim 438. As the cover is rotatably advanced toward a closed position, the sensor plunger 446 (FIG. 18) is advanced into the housing 448 until it reaches a point within the housing that is commensurate with complete cover closure, at which point an electrical signal is emitted from the sensor 444 to the control processor 420. Upon receipt of the sensor signal, the processor 420 transmits a signal to a solenoid 450 near the chamber inlet 415 to effect extension of a latch 452 from the solenoid housing 454 and into a correspondingly-dimensioned recess 456 formed in a latch receptacle 458 mounted to the exterior surface of the side 435 of the cover. Extension of the latch into the latch receptacle 458 is required before processing of waste material can proceed so as to ensure user safety from not only contamination with potentially infectious waste, but also from physical harm which could result from exposure to processed waste solids as they are returned under pressure to the decontamination chamber 402 following grinding. As a further precaution, the solenoid 450 is of the type which requires electrical signal input to effect either retraction or extension of the latch 452. Accordingly, the cover 414 is constructed so as to be incapable of being opened by ordinary means during the course of waste processing as well as in the event of a system or power failure during a material processing cycle, thereby ensuring that the cover is not opened until processing has been completed.

With reference once again to FIGS. 14-16, uncontaminated (i.e., fresh or non-potable) water is supplied to the reservoir or pre-heat tank 406 via supply line 462 for subsequent use in the sterilization process. Water is conveyed from the supply line 462 into the pre-heat tank 406 by an inlet pipe 464 when a control valve 466 such as a solenoid valve positioned in the inlet pipe 464 (FIG. 15) is biased in an "open" position. The valve 466, as is the case with all remotely controllable valves and pumps used in the system of the present invention, communicate in a conventional manner with the CPU 420 and receive operating instructions therefrom as indicated by communication line 465 (FIG. 14), unless the specification explicitly or implicitly provides otherwise. Valve 466 is further operable to effect a pressure reduction in the incoming water stream from conventional inlet pressure (typically 60 psi) to about 8 psi. Another solenoid valve 468 is provided in the supply line 462 downstream from the pipe 464 to control water flow into the cool-down tank 408. The valves 466 and 468 are independently operable to provide for the control of fluid flow into their respective tank. A pressure relief valve 470 and fluid backflow preventer 472, as well as various other conventional plumbing apparatus that are conventionally used in fluid management, are also provided along the water supply line 462.

The pre-heat tank 406 is preferably in the form of a large capacity electric or gas-fueled water heater that is operable in a conventional manner, such as through the use of a thermostatically controlled burner or heater assembly, to maintain the stored water at an elevated, stand-by temperature of about 170° F. (77° C.) so as to expedite waste processing in the manner described below. A conduit 474 extends between the pre-heat tank 406 and the pump inlet conduit 416 to provide for the delivery of fluid from the pre-heat tank 406 to the flow of waste material en route to the pump grinder assembly 410 when the system 400 is in operation. Water flow through the conduit 474 is controlled by a solenoid valve 476 in accordance with CPU 420 signal output in the manner described above. A pair of ventilation outlets 478 and 480 extend from the upper end of the pre-heat tank 406. A solenoid valve 482 is positioned in the outlet 478 to provide for controlled venting of pressure within the pre-heat tank 406, whereas ventilation outlet 480 is provided with a mechanical pressure-responsive relief valve 484 that is operable in emergency situations to vent pressure from the tank 406 when the valve's trigger pressure has been attained. As the valve 484 does not communicate with the CPU 420, it is isolated from any problems that may arise with system electronics; instead, it is responsive solely to pressure exerted against it in its associated outlet 480.

The decontamination chamber 402 is configured as a pressurizable vessel that is capable of withstanding pressures in the range of from about 55 psi to about 65 psi. The chamber 402 can be formed from any suitable material that is capable of withstanding the extremes of temperature, pressure and abrasion that are associated with operation of the system. Suitable materials include, by way of example, stainless steel alloys and high impact, high temperature plastics. Prior to the commencement of waste processing, pressure within the decontamination chamber 402 can be equalized with atmospheric pressure to facilitate filling of the preheat and cool-down tanks 406 and 408. This can be accomplished by opening the normally closed solenoid control valve 486 in vent pipe 488 that extends from the decontamination chamber.

The decontamination chamber is oriented vertically as shown in the drawings to make use of gravity to assist in feeding of the waste to the pump assembly 404 and to minimize spatial demands. Tank support legs 490 can be provided to elevate the chamber above the ground and to position its outlet 492 at the lower end of the chamber at a level substantially even with that of the entrance to the pump inlet conduit 416.

With reference to FIGS. 14-16, a plurality of heaters 494 are provided at the upper end of the decontamination chamber 402 to provide for heating of the water from its elevated base temperature of about 170° F. (77° C.) as stored in the storage tank 406 to the optimal operating temperature of from about 270° F. (132° C.) to about 275° F. (135° C.) during the course of system operation in the manner set forth in detail below. The heaters are preferably in the form of electric resistance immersion heaters having a power output of about 5,000 watts each. However, the number and power output of the heaters 494 can be varied in accordance with such factors as the quantity and composition (i.e., solid, liquid, plastic, metal and so on) of the waste that is expected to be typically processed by a system user, as well as the rate of processing (i.e., system through-put) that is required by the user. The temperature and pressure within the decontamination chamber is sensed by respective temperature and pressure sensors 496 and 498, (FIG. 14) the output of which is directed to the CPU 420, which is operable to adjust various system operation parameters in the manner described below in instances where signal output from one or both of the sensors 496 and 498 is indicative of a measured value outside of a range of prescribed system limits. A further pressure sensor, designated by reference character 500, is provided with the decontamination chamber 402 to provide for deactivation of the fluid heaters 494 in the event that sensed pressure within the chamber exceeds a predetermined value. Output from the pressure sensor 500 is conveyed locally rather than through the CPU 420 to the heaters 494 in a manner known in the art (such as by way of circuit interruption to disable the supply of electric current to the heaters) to effect their deactivation. Fluid level sensors 502 and 504 are provided at the upper end of the decontamination chamber 402 to respectively monitor fluid levels within the chamber. Sensor 502 provides signal output to the control processor 420 to effect termination of the supply of water from the hot water tank 406 to the pump inlet conduit 416 when the decontamination chamber fluid level reaches a prescribed maximum. Sensor 504 is operable to provide signal output for deactivating the heaters 494 when the fluid level within the chamber 402 diminishes below a prescribed level.

Figure 19:
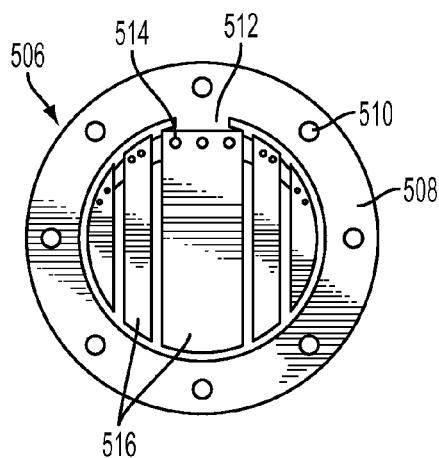
FIG. 19 is a frontal view of a waste control gate that can be positioned adjacent to the waste decontamination chamber outlet according to an embodiment of the present invention.

As noted above, waste from the decontamination chamber 402 passes from the chamber outlet 492 to the chopper/pump assembly 404 through pump inlet conduit 416. In the depicted embodiment, the conduit 416 is comprised of two sections 416a and 416b to accommodate the lateral displacement of the pump assembly 404 relative to the decontamination chamber; however, a greater or lesser number of sections can be provided in accordance with the system design. A gate 506 (FIGS. 14 and 19) is provided at the decontamination chamber outlet 492, preferably at the interface between the chamber outlet and the pump inlet conduit 416, to control the passage of waste to the pump assembly. The gate 506 is preferably constructed so that all of its moving parts are maintained within the sterilization fluid flow in order to ensure complete sterilization of the gate during the course of waste processing. With reference to FIG. 19, the gate 506 is shown as being comprised of a generally annular gasket 508 that is formed from a high temperature resistant material such as a "Viton" elastomer.

A plurality of apertures 510 are provided about the annular periphery of the gasket to receive therethrough appropriate fasteners such as bolts or rivets (not shown) that are used to secure the gate between the chamber outlet 492 and the waste conduit 416. A gasket tab 512 extends radially inwardly from a portion of the gasket 508 to which is secured in a conventional manner, as by rivets 514 or a suitable temperature resistant adhesive, a plurality of vertically arrayed bars 516. Because the gate bars 516 are secured to the tab 512 independently of one another, each is free to independently move to permit for the passage of waste material through the gate and to the chopper/pump assembly 404. The gate bars 516 can be provided with a generally flat or curved surface contour in their downstream (i.e., facing the viewer) direction in accordance with user preference to facilitate receipt within the curved interior of the pump inlet 416. The bars are formed from a temperature resistant, hardened material such as stainless steel or any other suitably hard and temperature and abrasion resistant material and are spaced up to several mm. apart from one another to restrict passage of waste solids of a size in excess of the bar separation distance from passing through the gate to the pump assembly until the combination of fluid pressure upstream of the gate 506 (i.e., within the decontamination chamber 402) and vacuum pressure developed by operation of the chopper/pump assembly 404 as described below overcomes the inertia provided by the gate.

The chopper/pump assembly 404 can be of any suitable design which provides the requisite degree of waste material processing (i.e., grinding and chopping) and flow to accomplish the desired objective of processing of waste into relatively small fragments, thereby increasing its surface area for contact with high temperature water for effecting disinfection and optimally sterilization. In preferred aspects of system operation, the chopper/pump 404 is operable to process solid waste to a size in the range of from about 1/16 in. (1.5 mm) to about 1/4 in. (6.5 mm) to not only facilitate its exposure to the heated fluid, but also to reduce waste volume. The family of horizontal endsuction chopper pumps manufactured by the Vaughan Co., Inc. of Montesano, Wash., such as the model VP3E pedestal pump, are particularly applicable for use in the present invention. Use of this family of pumps is advantageous, because their respective motors 412 are oil cooled and lubricated, thereby ensuring that waste contaminated water is confined to the prescribed waste and fluid circulation path. However, other motors which provide suitable amounts of torque, power, and confinement of the circulated fluid can be used.

Figure 20:
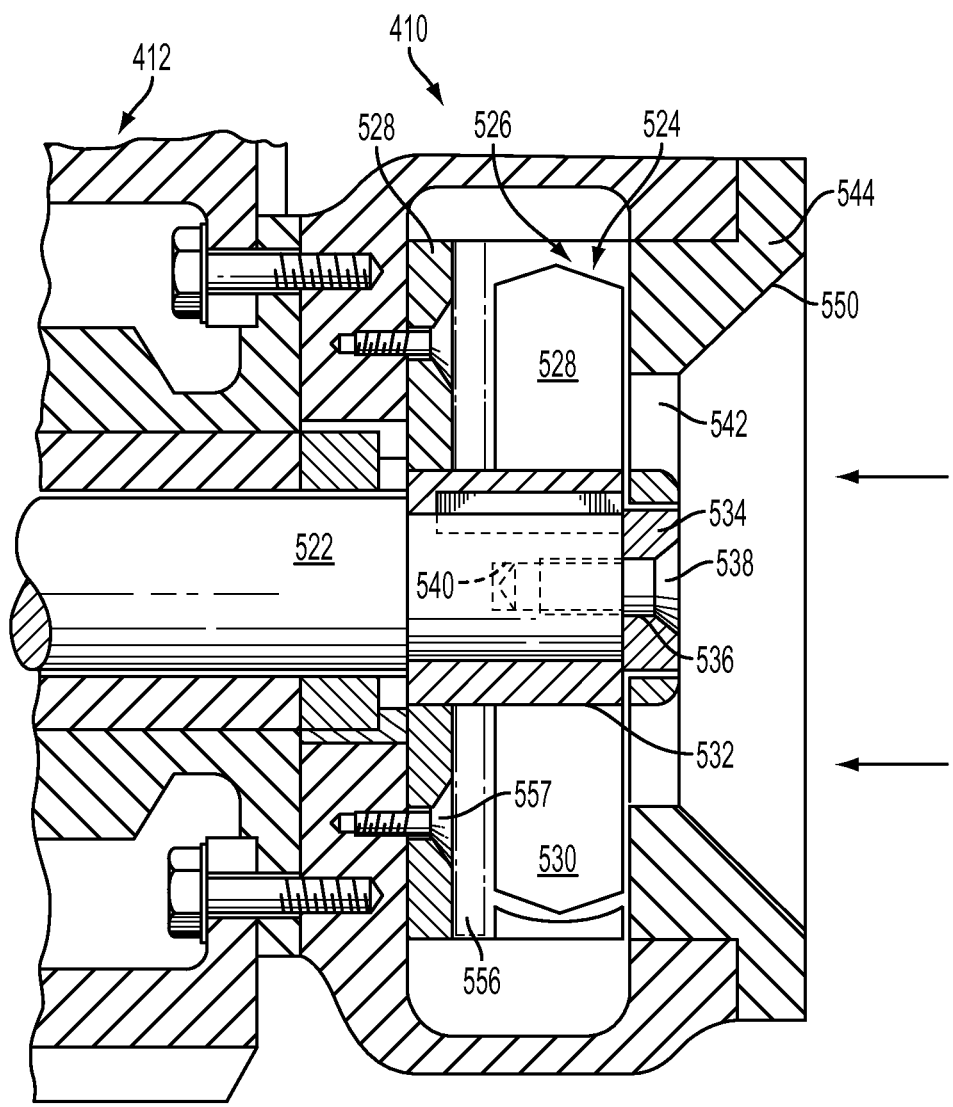
FIG. 20 is a sectional side view of a portion of the system pump assembly according to an embodiment of the present invention.
Figure 21:
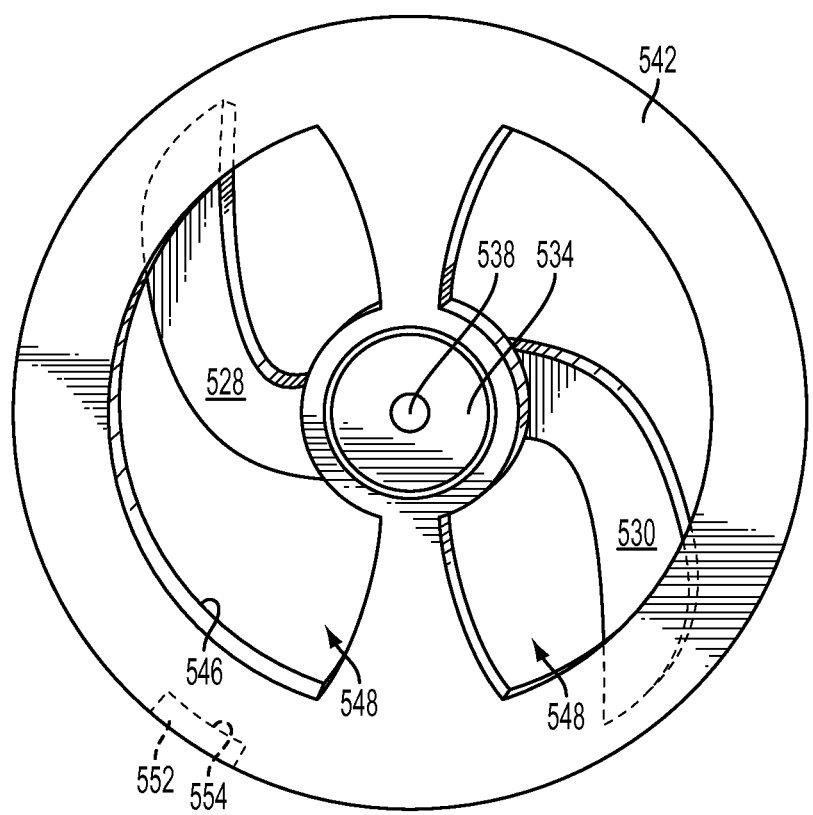
FIG. 21 is a frontal view of a portion of the system pump assembly according to an embodiment of the present invention.

With particular reference to FIGS. 20 and 21, further details of the grinder and motor assemblies 410 and 412 are provided. The motor output shaft 522 extends into the grinder assembly 410 to provide rotational driving input (through an appropriate gear reduction assembly (not shown)) to an impeller 524 that is rotatably received within a venturi-shaped materials processing chamber 526. The impeller 524 includes a blade assembly that is comprised of a pair of generally opposed, curvalinear cutter blades 528 and 530 that extend from a hub 532. The hub is fixedly secured to the free end of the motor output shaft 522 by a retaining plate 534 having an aperture 536 through which extends a conventional fastener, such as the depicted threaded fastener 538. The fastener 538 is received within a complementary-threaded and dimensioned recess 540 formed in the motor shaft 522.

Positioned upstream (i.e., to the right side in FIG. 20) of the cutter blades 528 and 530 is a cutter plate 542 that is fixedly positioned with respect to the surrounding grinder housing 544. Alternatively, the cutter plate and grinder housing can be configured as a one piece, integral unit. The lower surface 546 of the cutter plate is provided with a hardened sharpened surface that is positioned in close proximity to the rotatably driven cutter blades 528 and 530 to provide for a compound cutting action of waste material that is interposed between the blades and the cutter plate surface. The cutting plate 542 defines a pair of laterally spaced elongated passages or apertures 548 through which waste material passes for cutting by the cutting blades 528 and 530. The housing 544 defines a wall 550 along its medial surface which extends radially outwardly in the upstream direction so as to guide waste material and fluid to the cutter blades. Cutting efficiency is further enhanced by the provision of a cutter block 552 (FIG. 21) along a portion of the inner periphery of the materials processing chamber 526. The radial inner edge 554 of the cutter block is provided with a sharpened surface which, together with the fixed cutting edge 546 of the plate 542, provides for enhanced cutting efficiency, as waste material is engaged, cut, and hurled forcefully thereagainst by the rotatably driven cutter blades 528 and 530. Cutting efficiency can be further augmented by the provision of an auxiliary cutting plate 556 (depicted in phantom in FIG. 20) downstream of the cutter blades which can be provided with any of a variety of suitable configurations which supplements the cutting effectiveness of the rotatably driven blades 528 and 530. The auxiliary plate can be fixedly secured by threaded fasteners 557 or other suitable fastening means to the base 558 of the materials processing chamber 524 as shown, or can be elevated and supported therefrom by appropriately dimensioned spacers (not shown) in instances where the auxiliary cutting plate is provided with cutting passages of the type described above with reference to cutting plate 542.

In one aspect of the invention, the motor is operable to rotate the blades 528 and 530 at a variety of different speeds (typically in the range of from about 1700 rpm to about 1900 rpm) in accordance with the waste composition (i.e., liquids, textiles, metals and so on) and such user-selectable parameters as flow rate through the system. Alternatively, a single motor speed can be provided for processing the waste without regard to its composition. Waste processing in both schemes of operation is to continue for so long as necessary to ensure that the waste is exposed to superheated water (i.e., temperature exceeding 270° F. (132° C.)) for a minimum of six minutes or longer in instances where waste sterilization is to be effected, as will be described in greater detail below. Because a variety of different types of waste are capable of being handled by the waste processing system of the present invention, all cutting surfaces are formed from suitably durable materials, such as hardened metal alloys and/or metals provided with a suitable chemical coating in a manner well known in the field of metallurgy.

With reference again to FIGS. 14-16, ground waste material and fluid processed by the grinder assembly 412 is urged through the materials processing chamber 526 to the decontamination chamber through grinder outlet 418, thereby providing a closed system for continued waste processing in the manner to be described below. During the course of system operation, the fluid heaters 494 are activated to elevate the temperature of the water and entrained waste material to the desired operation temperature (from about 270° F. (132° C.) to about 275° F. (135° C.) to effect sterilization) and the pump 412 is operated for a period in excess of the requisite period of time that is accepted for effecting the desired disinfection or sterilization (in accordance with user instructions) in order to ensure sterilization of not only the waste material and fluid, but all of the waste processing hardware with which the waste and fluid comes into physical contact. The closed fluid path is maintained at a pressure of from about 55 psi to about 65 psi to ensure that the water introduced into the system for effecting sterilization maintains substantially a liquid state of matter. As mentioned above, sterilization with liquid water rather than water vapor is preferred to ensure full contact and penetration (where applicable) of waste solids to effect sterilization of even compact, porous materials such as textiles and gauze which can readily absorb potentially infectious bodily fluids. Excess pressure can be vented from this closed system into the cool-down tank through the operation of valves 518 and 519 (FIG. 15). Valve 518 is positioned in vent pipe 520 which extends between the decontamination chamber 402 and the cool-down tank 408 and is in the form of a self-actuating pressure relief valve that is operable to open and permit communication between the chamber and tank 408 once its set pressure has been attained. Valve 519, which is positioned in line 521 which branches from pipe 420 to the cool-down tank, is a solenoid valve under the control of the CPU 420 and is operable during the waste material cool-down cycle described below to release pressure from the decontamination chamber 402.

Once the prescribed period for waste sterilization in the system has passed, the sterilized liquid and entrained waste solids (collectively referred to as "waste mixture") are directed to the cool down tank 408 from the decontamination chamber 402 through inlet pipe 566. Flow into the inlet pipe 566 is controlled by solenoid valve 568, which is ordinarily biased in a closed position to prevent premature cooling of the waste material prior to completion of the required disinfection or sterilization cycle. As the waste mixture is received within the cool down tank 408, cool water contained within the tank 408 is admitted into the decontamination chamber 402 along conduit 570 (FIG. 14). A fluid pump 572 is provided in the conduit 570 to supply a pressurized flow of cooling water to the decontamination chamber. A valve 574 such as a ball valve is provided in the conduit to ensure unidirectional fluid flow into the decontamination chamber once the pump 572 has been activated. As the waste mixture is circulated by the pump assembly 404 throughout the closed system and cool down tank, the mixture is cooled from the temperature that was necessary to ensure the desired disinfection or sterilization to a temperature which satisfies any prevailing municipal requirements for waste disposal into, for example, a municipal sewer system. Once the temperature of the cooled waste mixture has diminished to the requisite disposal temperature, it is directed by the operation of pump 572 (FIG. 14) from the cool down tank, upon opening of solenoid valve 578, through a disposal conduit 576 (FIG. 15) for removal from the processing system. Preferably, the waste solids are separated from the liquid, as can be accomplished by filtration through filter assembly, depicted in phantom and denoted generally by reference character 580, prior to disposal, thereby reducing by several orders of magnitude the volume of waste solids to be disposed for many waste materials.

System Operation

Figure 22:
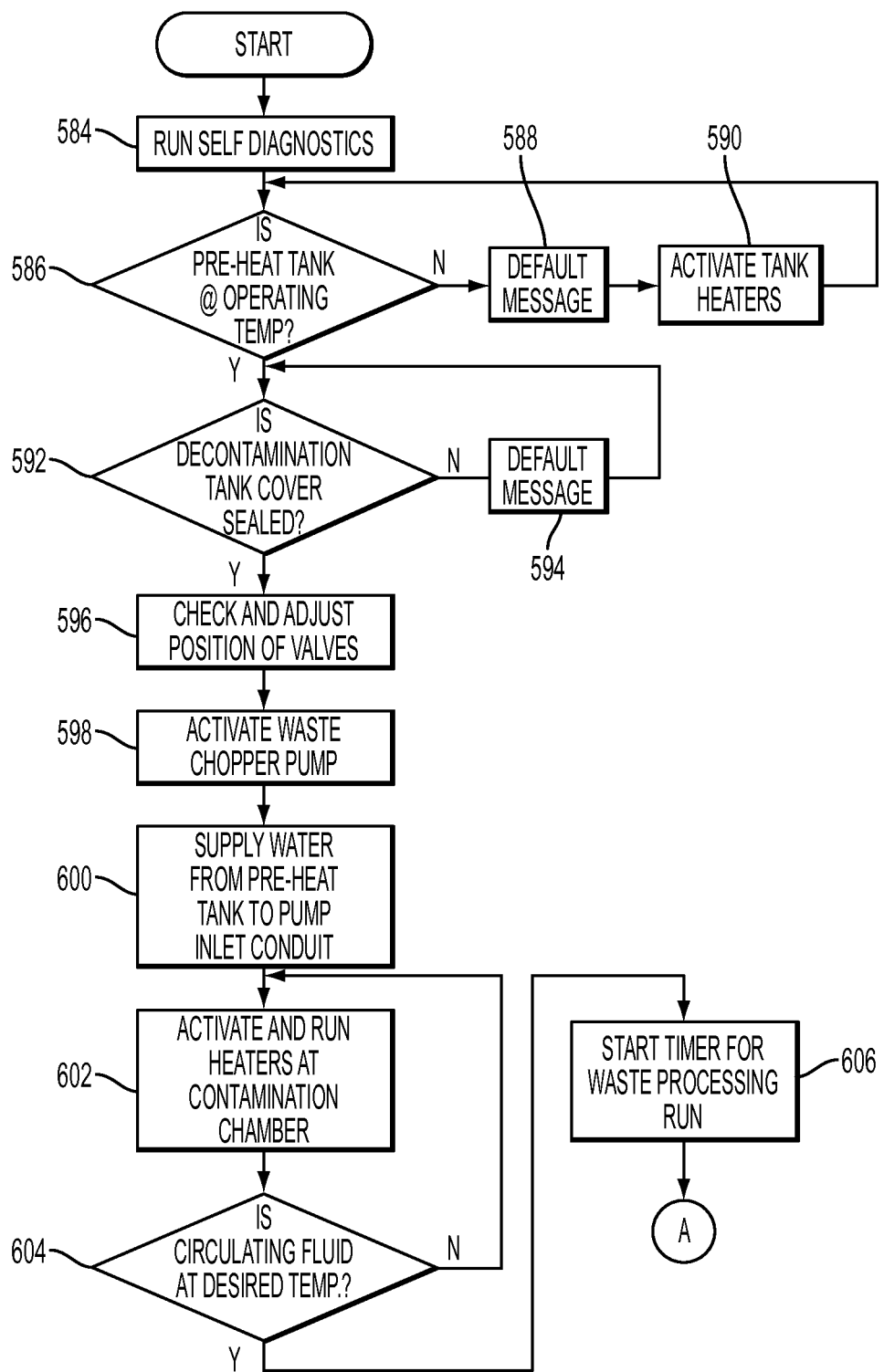
FIG. 22 is a flow diagram of the operational control arrangement for the present invention.
Figure 23:
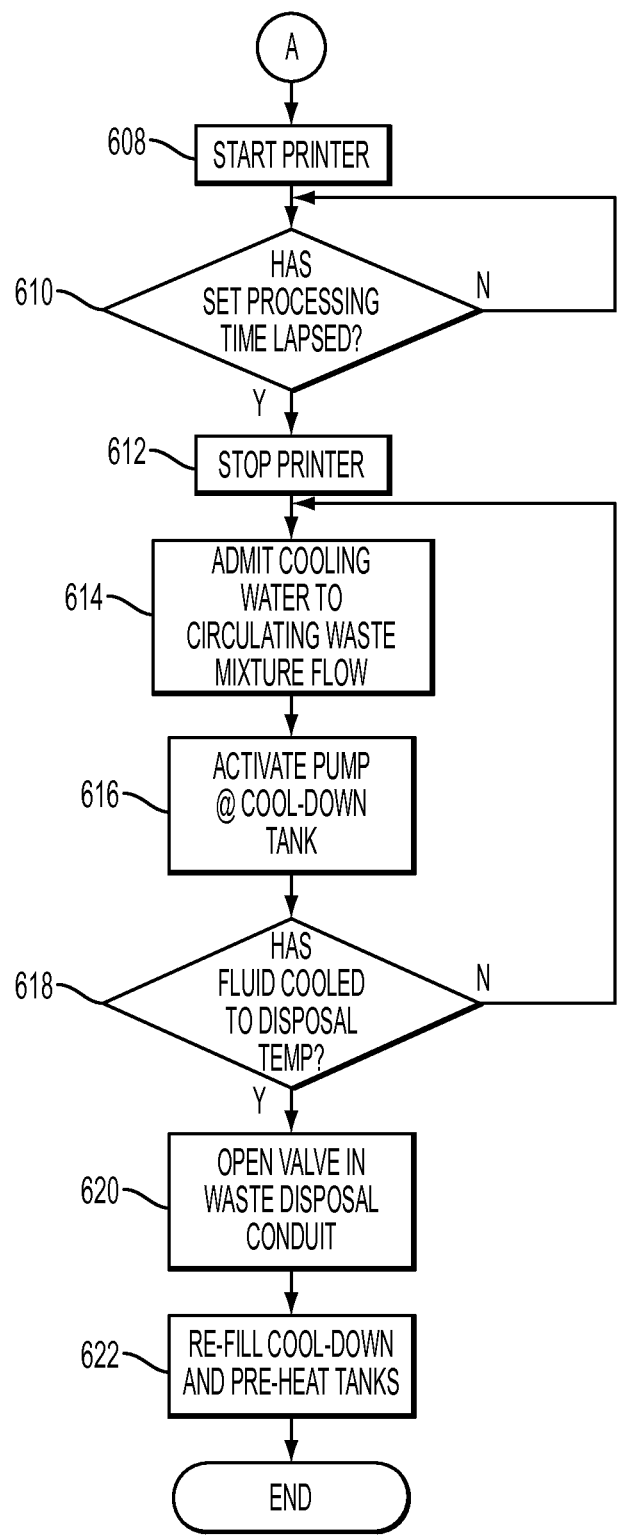
FIG. 23 is a flow diagram of the operational control arrangement for the present invention.

The operation of the waste processing system 400 of the present invention will now be described with reference to the flow diagram illustrated in FIGS. 22 and 23, with concurrent reference to FIGS. 14-16.

Waste to be processed is deposited in the decontamination chamber 402 and the lid 414 therefor is closed and sealed. Prior to the commencement of waste processing, the CPU 420 is operable in accordance with program control from RAM to run a self-diagnostic check of the system electricals and electrically-operated components such as various valves and temperature and pressure sensors which communicate with the CPU, as indicated by block 584 in the flow chart. Communication between such electrically operable components and the CPU is indicated in FIG. 14 by a communication line extending between the controlled part and the CPU. An example of such a communication line is provided by line 465 which extends between valve 466 and the CPU 420. It is to be understood, however, that similar communication lines exist between the CPU 420 and each part of with which the CPU communicates, either in a unidirectional or a bi-directional manner. For the sake of clarity, however, such lines have not been included in FIG. 14, but they are understood to be present in order to provide the requisite control for system operation as described previously and below.

Upon successful completion of the self-diagnostic test, the CPU 420 receives signal input from a temperature sensor included with the pre-heat tank 406 that provides an indication of the temperature of fluid within the tank, as indicated by decision block 586. In instances where fluid temperature is below prescribed system operating limits for the system 400, as may be the case when the tank has recently been replenished with tap water, a "default" message conveying to the system user the unreadiness of the system to commence operation is produced in the display 426, as indicated by block 588, and the heating elements included with the tank are switched on to bring the fluid stored within the tank to operating temperature, noted by block 590.

In instances where the pre-heat tank fluid temperature meets the pre-established operating temperature, the CPU 420 is then commanded to analyze input from the decontamination chamber cover solenoid 454 (FIG. 18) to determine whether or not the cover 414 has been properly sealed, as shown by block 592. An appropriate default message such as "close cover" (block 594) is generated for display to the user via console display 426 in instances where output from the solenoid 454 to the CPU 420 along an appropriate communication line (not shown) is indicative of incomplete cover closure. If the output from the solenoid 454 is of a character that confirms cover closure and sealing, the CPU 420 is operable to communicate with the various valves and pumps under its control to confirm their respective proper orientation (i.e., "closed" or "open") prior to commencement of system waste handling (block 596) and to adjust the valves accordingly in instances where the valve position or pump operation status communicated to the CPU 420 does not comply with the system operating program stored in RAM 422.

Once the foregoing system operation statuses have been confirmed and corrected as required, the CPU 420 is operable to deliver signal input to the chopper/pump assembly 404 to effect chopper/pump operation at the prescribed rate of speed (block 598) and to deliver signal input to the valve 476 to permit a flow of heated fluid from the pre-heat tank 406 to the pump inlet conduit 416 (block 600). Fluid delivered from the tank 406 is conveyed by the chopper/pump 404 to the decontamination chamber 402 through pump outlet 418, where the fluid mixes with the waste material deposited therein. Once fluid pressure within the decontamination chamber 402, in combination with the negative pressure exerted by the chopper/pump 404, exceeds the inertia of the waste gate 506, waste solids pass with the fluid flow to the chopper/pump grinder assembly 410, where they are chopped and ground by the rotating cutter blades 529 and 530 and cooperating cutting surfaces of the cutter plate(s) 542 and 556, and conveyed into outlet 418 for recirculation to the decontamination chamber 402. Fluid level sensor 502 provides signal output to the CPU to convey the fill status of the decontamination chamber as water is delivered from the pre-heat tank into the circulating stream of water and liquid and solid waste material in the manner described above.

As the fluid and waste mixture is circulated between the decontamination chamber and chopper/pump through the respective pump inlet and outlet conduits 416 and 418, the CPU 420 is operable to activate the decontamination chamber heaters 494 (Block 602) to elevate the temperature of the circulating stream to the operating temperature that is required to effect the selected level of processing. In this regard, a temperature in the range of 270° F. is to be maintained for a continuous period of at least six minutes to effect waste sterilization, whereas a lesser temperature on the order of at least about 212° F. is preferred for disinfection. Temperature data from the decontamination chamber is conveyed by sensor 496 to the CPU, which continues signal output to the heaters 494 (block 604) until the fluid temperature as sensed by sensor 496 reaches the desired operating temperature. Once this temperature has been attained, a timer (not shown) such as that typically provided for CPU operation is started, as noted by block 606. Additionally, a printer, which can optimally be provided with the system to document such system parameters as fluid temperature, is also actuated (block 608).

As the waste processing cycle continues in the foregoing manner, the CPU is operable to compare clock and temperature sensor 496 output data with the preselected time and temperature parameters stored in CPU memory to allow for determination of whether the required time of material processing at the requisite temperature set forth in the CPU operating program has lapsed (block 610). This comparison process continues until the clock and temperature data provided to the CPU 420 indicate that the requisite period has passed, at which time the printer is deactivated (block 612) and the CPU is operable to effect cooling of the water and entrained waste solids and liquids ("waste mixture") as indicated by block 614.

The CPU 420 implements cooling of the waste mixture by directing valve 574 in the cooling tank conduit 570 to open and pump 572 to commence pumping of cool (i.e., ambient temperature or chilled) water into the decontamination chamber 402, as indicated by block 616. The CPU 420 also commands valve 568 in inlet 566 to open, thereby admitting a portion of the circulating waste mixture with the cool-down tank 408. The CPU monitors the temperature of the circulating waste mixture (block 618) and continues to supply cool water until the temperature diminishes to the desired level for disposal. The desired cooling temperature may, for example, be that temperature established by municipalities at which qualifying waste material can be passed into the sewer or other municipal disposal system. Once the temperature has reached the requisite cool-down temperature, the CPU 420 directs waste valve 578 in disposal conduit 576 to open (block 620), thereby allowing for the disposal of the cooled waste mixture from the cool-down tank 406. Waste solids in excess of a predetermined size can optionally be filtered from the waste mixture passing through the disposal conduit to permit its disposal apart from the liquid component of the waste mixture. Such waste solids, by virtue of having been processed in the foregoing manner, can be disposed of in a conventional manner in a compact form, thereby lessening the burden on waste disposal facilities and on the waste originator in providing for safe and efficient waste disposal. The CPU is operable thereafter to provide for refilling of the respective pre-heat and cool-down tanks (Block 622) to replenish their supplies of water used in the foregoing processing cycle. Tank refilling is accomplished as a result of CPU signal input to valves 466 and 468 directing their respective opening, thus allowing for replenishment of associated pre-heat and cool-down tanks 406 and 408 with fresh water for use in a subsequent waste processing cycle.

Figure 24:
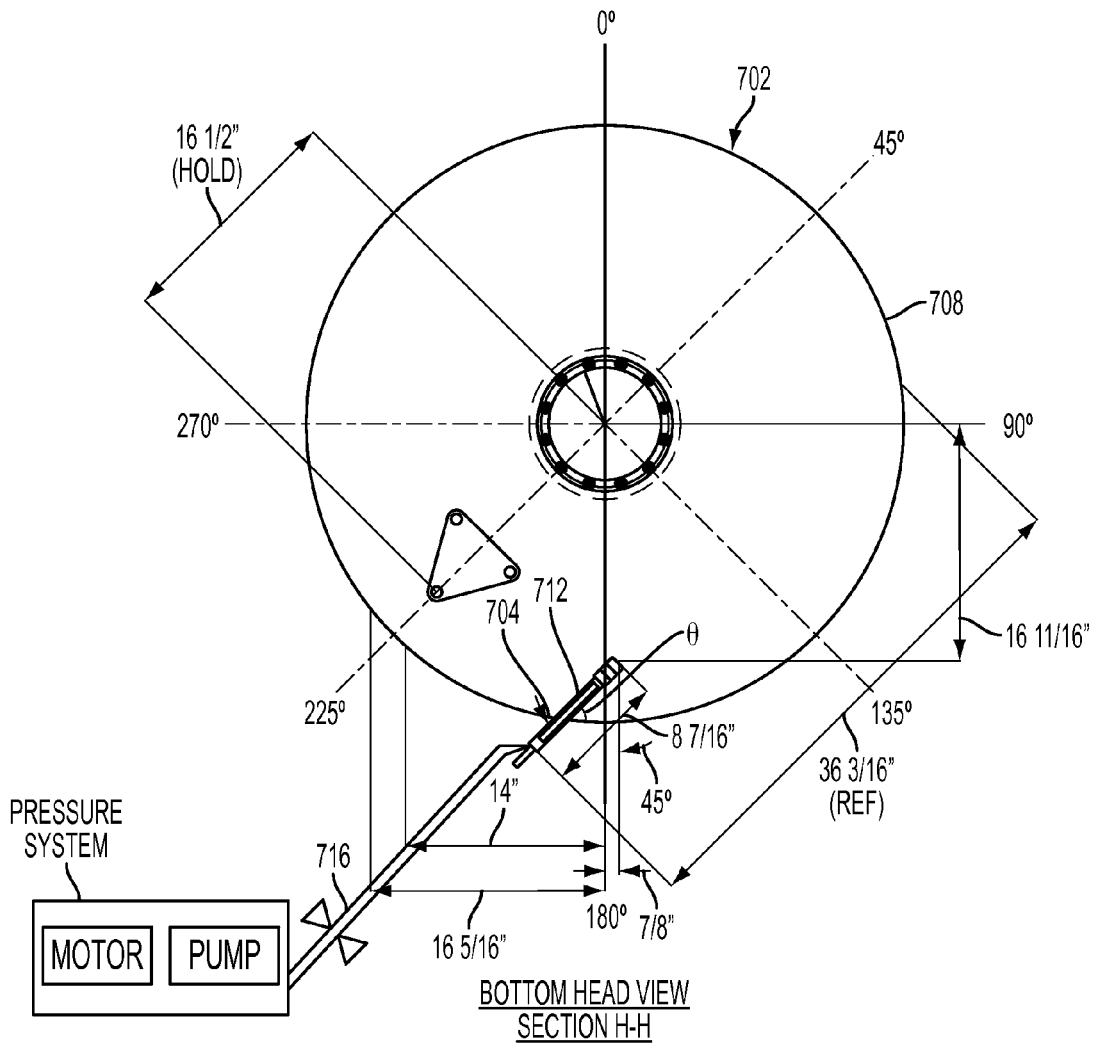
FIG. 24 is a schematic of a bottom view of a receptacle of a waste processing system according to an embodiment of the present invention.
Figure 25:
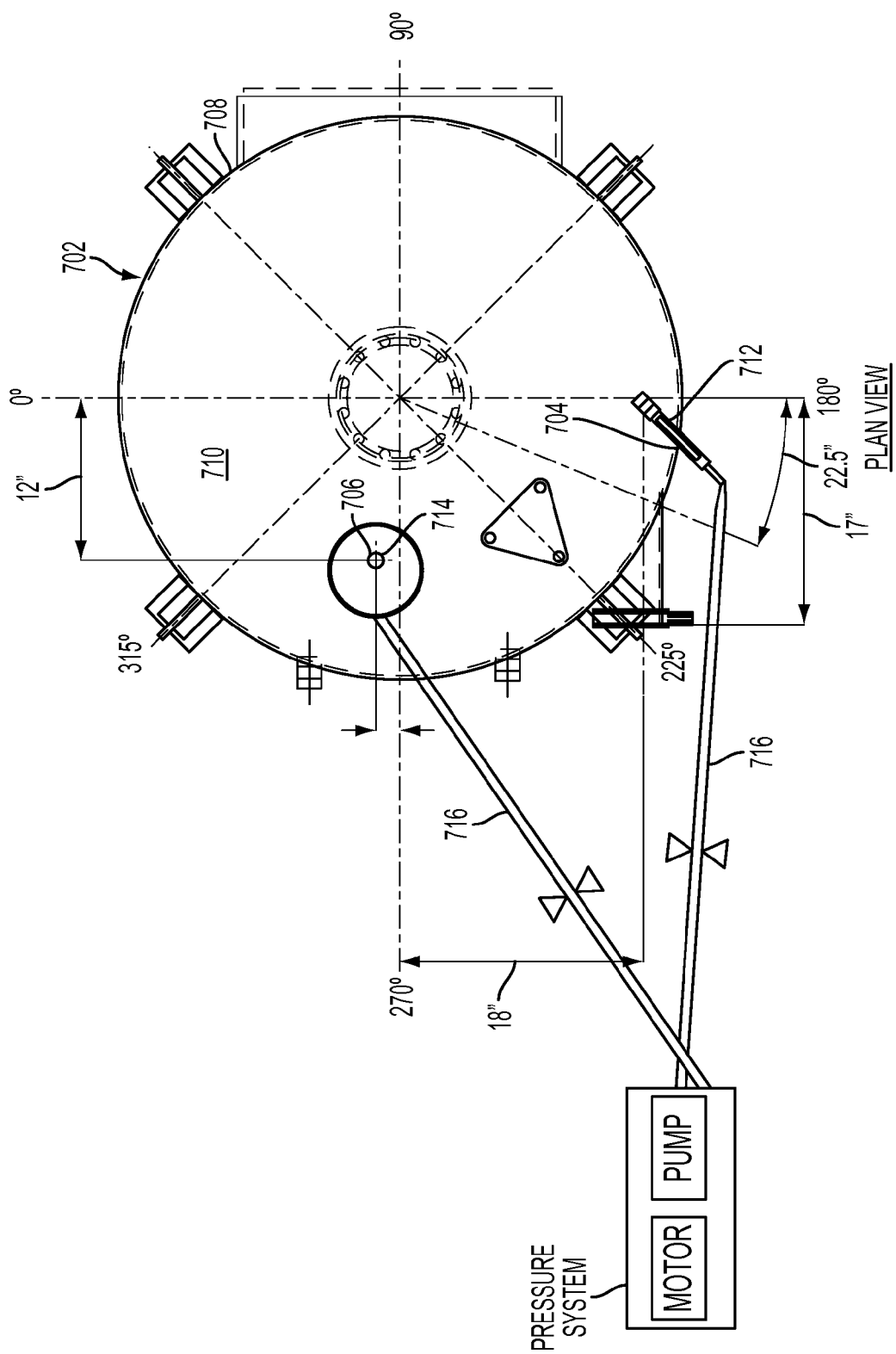
FIG. 25 is a schematic of a plan view of the receptacle shown in FIG. 24 according to an embodiment of the present invention.
Figure 26:
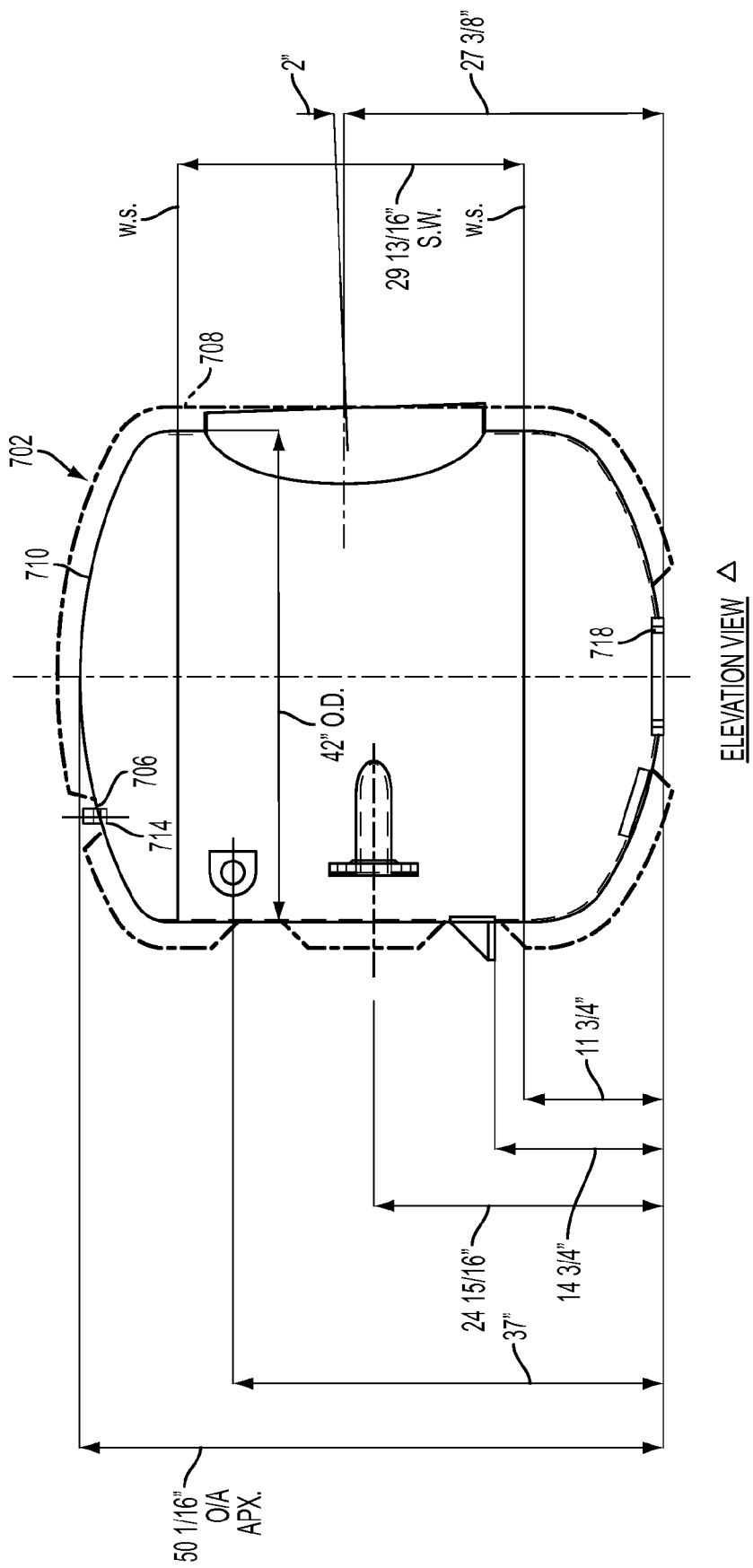
FIG. 26 is a schematic of an elevation view of the receptacle shown in FIG. 24 according to an embodiment of the present invention.

According to embodiments of the present invention, the waste processing system may include a receptacle 702 that includes one or more nozzle openings 704, 706, as shown in FIGS. 24-26. FIGS. 24 and 25 show a bottom and top view, respectively, of the receptacle 702. FIG. 26 shows an elevation view of the receptacle 702. A nozzle opening 704 is shown in the cylindrical side wall 708 of the receptacle 702 and a nozzle opening 706 is shown in the top surface 710 of the receptacle 702. Embodiments of the present invention are not limited to the configuration of nozzle openings shown in FIGS. 24-26 and may include more or fewer nozzle openings and/or differently positioned nozzle openings.

Therefore, a waste processing system according to an embodiment of the present invention may include the receptacle 702 for receiving waste material, including bags of waste, and a liquid to be mixed with the waste material. The receptacle 702 may also have an inlet and a waste outlet, similar to the above-discussed embodiments. The nozzle openings 704, 706 are adapted to receive slicing nozzles 712, 714 that spray a slicing fluid (not pictured) under pressure into the receptacle 702 via the nozzle openings 704, 706. Though FIG. 25 shows two slicing nozzles 712, 714, more or fewer slicing nozzles may be provided.

A pressure system may also be provided that pressurizes the slicing fluid. The pressure system and the slicing nozzles 712, 714 produce a spray sufficient to manipulate the waste material. For example, the spray may be sufficient to move the waste material in one or more directions within the receptacle 702. Additionally, the spray may be of sufficient pressure and character to slice open bags or other containers that contain waste (e.g., "red bags"). Accordingly, containers or bags of waste may be efficiently opened while within the receptacle 702, allowing the waste contained therein to be more effectively treated by the waste processing system. The pressure system may include, for example, a pressure pump (not pictured) and a motor (not pictured) to run the pressure pump. The pressure pump may be able to supply the slicing fluid at a pressure of at least 2,000 psi within the receptacle, or at a pressure of at least 3,000 psi within the receptacle. Pressure hoses 716 and valves may connect the pressure pump to the slicing nozzles 712, 714 to operate the slicing nozzles at predetermined pressures. The slicing nozzles 712, 714 may be arranged to produce or direct the spray such that the spray is capable of slicing open bags of waste. For example, the spray may be a fine, needle-like spray.

The slicing nozzles 712, 714 may further be arranged at an angle θ relative to a wall of the receptacle 702 such that a direction of the slicing spray contributes to movement of the waste material within the receptacle 702. For example, the spray from one or more slicing nozzles may contribute to a circulatory motion of the waste material within the receptacle 702 and/or to a movement of the waste material toward a waste outlet 718. In some configurations, the slicing nozzle 712 may contribute to the circulatory motion and the slicing nozzle 714 may contribute to the motion of waste material toward the waste outlet 718. Alternatively, one or both slicing nozzles may contribute to both of these types of motion.

In some embodiments, the slicing nozzles 712, 714 may be arranged at an angle with respect to the receptacle 702, which can aid in directing the motion of the waste material. The slicing nozzle 714 in the top surface 710, for example, may be arranged at an angle ranging from 15 to 35 degrees relative to the top surface 710. The slicing nozzle 712 in the cylindrical side wall 708, for example, may be arranged at an angle ranging from 30 to 60 degrees relative to a portion of the cylindrical side wall 708 in which the nozzle opening 704 is formed.

The waste processing system may also include a pump, with a pump inlet and an outlet, for chopping the waste material and circulating and mixing the liquid and waste material. A waste inlet conduit may extend between the waste outlet and the pump inlet, and a waste outlet conduit may extend between the pump outlet and the receptacle inlet. The receptacle, pump, waste inlet and waste outlet conduits may define a closed, pressurized waste processing circuit through which the mixed liquid and waste material can be circulated. Additionally, a heating system may heat the mixture of the liquid and the waste material to a temperature in excess of the boiling point of the liquid at standard pressure. The temperature can be sufficient to effect biological neutralization of the mixed liquid and waste material, and all surfaces of said waste processing system with which the waste material comes into contact may be processed to attain said biological neutralization. Details of the immediately preceding features have been discussed elsewhere above, and will not be repeated here for brevity.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for caring out this disclosure. Moreover, features described in connection with one embodiment of the invention may be used in conjunction with other embodiments, even if not explicitly stated above.

I hereby claim:

1. A waste processing system, comprising:
   a receptacle for receiving waste material, including bags of waste, and a liquid to be mixed with the waste material, said receptacle having an inlet, a waste outlet, and at least one nozzle opening;
   at least one slicing nozzle that sprays a slicing fluid under pressure into the receptacle via the at least one nozzle opening;
   a pressure system that pressurizes the slicing fluid, the pressure system and the at least one slicing nozzle producing a spray sufficient to manipulate the waste material;
   a pump for chopping the waste material and circulating and mixing the liquid and waste material, said pump having a pump inlet and an outlet;
   a waste inlet conduit extending between said waste outlet and said pump inlet;
   a waste outlet conduit extending between said pump outlet and said receptacle inlet, said receptacle, pump, waste inlet and waste outlet conduits defining a closed, pressurized waste processing circuit through which the mixed liquid and waste material can be circulated; and
   a heating system operable to heat the mixture of the liquid and the waste material to a temperature in excess of the boiling point of the liquid at standard pressure, said temperature being sufficient to effect biological sterilization of the mixed liquid and waste material, all surfaces of said waste processing system with which the waste material comes into contact being processed to attain said biological sterilization.

2. The system according to claim 1, wherein the manipulating of the waste material includes at least one of directing movement of the waste material within the receptacle and opening the bags of waste.

3. The system according to claim 1, wherein the pressure system includes a pressure pump and a motor to run the pressure pump.

4. The system according to claim 3, wherein the pressure pump is configured to supply the slicing fluid at a pressure of at least 2,000 psi within the receptacle.

5. The system according to claim 4, wherein the pressure pump is configured to supply the slicing fluid at a pressure of at least 3,000 psi within the receptacle.

6. The system according to claim 1, wherein the at least one slicing nozzle produces a spray which manipulates the waste material.

7. The system according to claim 1, further comprising pressure hoses and valves between the pressure pump and the at least one slicing nozzle to operate the at least one slicing nozzle at predetermined pressures.

8. The system according to claim 1, wherein the at least one slicing nozzle is arranged at an angle relative to a wall of the receptacle in which the corresponding at least one nozzle opening is formed such that a direction of the slicing spray at least contributes to a circulatory motion of the waste material within the receptacle.

9. The system according to claim 1, wherein the receptacle comprises a top surface, a bottom surface and a substantially cylindrical side wall that define a substantially hollow chamber, and
   wherein the at least one nozzle opening includes a nozzle opening in the top surface of the receptacle.

10. The system according to claim 9, wherein the at least one slicing nozzle in the nozzle opening in the top surface is arranged at an angle ranging from 15 to 35 degrees relative to the top surface.

11. The system according to claim 9, wherein the at least on slicing nozzle in the nozzle opening in the top surface at least contributes to a movement of the waste material toward the waste outlet.

12. The system according to claim 1, wherein the receptacle comprises a top surface, a bottom surface and a substantially cylindrical side wall that define a substantially hollow chamber, and
   wherein the at least one nozzle opening includes a nozzle opening in the cylindrical side wall of the receptacle.

13. The system according to claim 12, wherein the at least one slicing nozzle in the nozzle opening in the cylindrical side wall is arranged at an angle ranging from 30 to 60 degrees relative to a portion of the cylindrical side in wall which the at least one nozzle opening is formed.

14. The system according to claim 12, wherein the at least one slicing nozzle in the nozzle opening in the cylindrical side wall at least contributes to a circulatory movement of the waste material within the receptacle.

15. The system according to claim 1, wherein the heating system comprises a liquid heater that is mounted within the receptacle.

16. The system according to claim 1, wherein the liquid comprises water and the heating system is operable to heat the liquid to a temperature of at least about 100° C.

17. The system according to claim 1, wherein said heating system comprises at least one temperature sensor operable to sense the temperature of the liquid and closed, pressurized waste material mixture circulating through said waste processing circuit.

18. The system according to claim 1, further comprising a processed waste storage receptacle.

19. The system according to claim 18, wherein said processed waste storage receptacle is coupled to said closed, pressurized waste processing circuit through a selectively operable valve.

20. The system according to claim 18, wherein said processed waste storage receptacle includes a discharge outlet.

21. The system according to claim 20, further comprising a waste solids filter positioned adjacent to said discharge outlet, said waste solids filter being operable to retain processed waste solids of a predetermined minimum size prior to discharge from the waste storage receptacle.

22. The system according to claim 1, further comprising a waste solids restrainer positioned within said closed, pressurized waste processing circuit, said waste solid restrainer being operable to inhibit downstream passage of waste solids in excess of a predetermined size until a predetermined pressure has been attained within said closed, pressurized waste processing circuit.

23. The system according to claim 22, wherein said waste solids restrainer comprises a plurality of pivotably displaceable strips.

24. The system according to claim 1, wherein said receptacle comprises a removable cover, said removable cover and said receptacle comprising a mutually engageable locking system that is operable to inhibit cover removal until waste has been processed for a prescribed time interval.

25. The system according to claim 1, further comprising a control system operable to receive temperature input data from said mixture of waste material and liquid circulating through said closed, pressurized waste processing circuit and to operate said pump for a prescribed time interval once said sensed temperature has attained a prescribed level.

26. The system according to claim 25, further comprising a processed waste receptacle and a selectively operable valve assembly mounted within a processed waste conduit extending between said processed waste receptacle and said closed, pressurized waste processing circuit, said control system being operable to move said valve assembly between an open position and a closed position.

27. The system according to claim 26, wherein said processed waste receptacle includes an outlet and a selectively actuatable valve assembly mounted in communication with said receptacle outlet, said control system being operable to move said selectively actuatable valve assembly between an open position and a closed position.

28. The system according to claim 26, further comprising a cooling fluid inlet conduit coupled to said closed, pressurized waste processing circuit, said control system being operable to selectively effect delivery of cooling fluid through said cooling fluid inlet conduit and into said closed, pressurized waste processing circuit.

29. The system according to claim 28, wherein said cooling fluid inlet conduit is coupled to a municipal water supply.

30. The system according to claim 25, wherein said control system is capable of operating said heating system to attain a temperature for the circulating mixture of waste material and liquid that is sufficient to effect sterilization of the mixture.

31. The system according to claim 25, wherein said heating system includes at least on fluid heater that is operable in accordance with signal input from said control system to maintain the liquid within the receptacle at a prescribed, elevated temperature.

32. A system for processing waste to a prescribed level of biological inactivity, comprising:
a receptacle for receiving waste material, the receptacle having a re-sealable cover, a fluid inlet, and a fluid outlet;
means for pressurizing a slicing fluid;
a slicing nozzle which sprays the slicing fluid when the slicing fluid is pressurized, thereby reducing the dimensions of the waste material and mixing the reduced waste material with the slicing fluid to form a liquid-waste mixture;
means for circulating the liquid-waste mixture within a closed, pressurized circuit including said receptacle and the slicing nozzle;
means for heating the liquid-waste mixture to a prescribed temperature above the boiling point of the liquid at standard pressure; and
control means for implementing selective operation of said slicing nozzle, said circulating means, and said heating means to effect waste processing at the prescribed temperature for a prescribed time interval to effect biological sterilization of the waste material and all surfaces of the waste processing system with which the waste material comes into contact.

33. The system according to claim 32, wherein the heating means is operable to heat the liquid-waste mixture within the closed, pressurized circuit.

34. The system according to claim 33, wherein said control means comprises at least one temperature sensor operable to provide signal output that is indicative of liquid-waste mixture temperature within the closed, pressurized circuit.

35. The system according to claim 34, further comprising means for discharging processed waste into a municipal waste removal system.

36. The system according to claim 34, further comprising means for separating waste solids of a predetermined minimum size from the processed liquid-waste mixture.

37. The system according to claim 34, further comprising means for reducing processed liquid-waste mixture temperature and for disposing of at least a portion of said processed liquid-waste mixture following attainment of a prescribed maximum liquid-waste temperature value.

38. The system according to claim 37, wherein said temperature reducing means comprises means for admitting a cooling liquid into said closed pressurized circuit.

39. The system according to claim 32, further comprising a processed waste storage receptacle.

40. The system according to claim 32, wherein said receptacle comprises means for inhibiting cover removal upon initiation of a waste processing cycle until said waste processing cycle has been completed.

41. The system according to claim 40, wherein said cover removal inhibiting means comprises a solenoid reciprocably extendible within a recess formed within said re-sealable cover.

42. The system according to claim 32, wherein slicing nozzle and said liquid-waste mixture circulating means comprises a rotatably drivable impeller mounted within said closed, pressurized circuit.

43. The system according to claim 32, wherein said control means is operable to effect heating of said liquid-waste mixture to a temperature of at least about 100° C.

44. The system according to claim 43, wherein said control means is operable to effect heating of said liquid-waste mixture to a temperature in the range of from about 130° C. to about 135° C. while said system is maintained at a pressure sufficient to substantially inhibit vapor formation.

* * * * *